(12) United States Patent
Pham

(10) Patent No.: US 11,589,803 B2
(45) Date of Patent: Feb. 28, 2023

(54) METHODS AND SYSTEMS FOR IMPROVING HUMAN FACIAL SKIN CONDITIONS BY LEVERAGING VEHICLE CAMERAS AND SKIN DATA AI ANALYTICS

(71) Applicant: TOYOTA MOTOR ENGINEERING & MANUFACTURING NORTH AMERICA, INC., Plano, TX (US)

(72) Inventor: Alexander T. Pham, San Jose, CA (US)

(73) Assignee: TOYOTA MOTOR ENGINEERING & MANUFACTURING NORTH AMERICA, INC., Plano, TX (US)

( * ) Notice: Subject to any disclaimer, the term of this patent is extended or adjusted under 35 U.S.C. 154(b) by 379 days.

(21) Appl. No.: 16/865,984

(22) Filed: May 4, 2020

(65) Prior Publication Data

US 2021/0338146 A1    Nov. 4, 2021

(51) Int. Cl.
| | |
|---|---|
| *G06T 7/00* | (2017.01) |
| *A61B 5/00* | (2006.01) |
| *A61B 5/18* | (2006.01) |
| *G06T 7/38* | (2017.01) |
| *B60R 11/04* | (2006.01) |

(52) U.S. Cl.
CPC .............. *A61B 5/441* (2013.01); *A61B 5/18* (2013.01); *A61B 5/7435* (2013.01); *B60R 11/04* (2013.01); *G06T 7/0014* (2013.01); *G06T 7/38* (2017.01); *A61B 2503/22* (2013.01); *A61B 2562/02* (2013.01); *G06T 2207/20081* (2013.01);
(Continued)

(58) Field of Classification Search
CPC ......... A61B 5/441; A61B 5/18; A61B 5/7435; A61B 2503/22; A61B 2562/02; A61B 5/0205; B60R 11/04; G06T 7/0014; G06T 7/38; G06T 2207/20081; G06T 2207/20084; G06T 2207/30088; G06T 2207/30252
USPC ........................................................ 600/306
See application file for complete search history.

(56) References Cited

U.S. PATENT DOCUMENTS

| | | | |
|---|---|---|---|
| 6,793,242 B2 | 9/2004 | Breed et al. | |
| 9,607,208 B2 * | 3/2017 | Hara ................. | A61B 5/0077 |

(Continued)

FOREIGN PATENT DOCUMENTS

WO    WO 2018/009219 A1    1/2018

*Primary Examiner* — Van D Huynh
(74) *Attorney, Agent, or Firm* — Oblon, McClelland, Maier & Neustadt, L.L.P.

(57) ABSTRACT

Facial skin analysis methods and systems for improving facial skin conditions using vehicle cameras of vehicles having onboard communication modules. Each vehicle is equipped to analyze the facial skin images over time periods and compare the images to determine skin conditions. Based on the facial skin conditions, a treatment recommendation can be transmitted to a seat occupant. Each vehicle is operatively connected to a facial skin analysis application in a data center. The facial skin analysis application includes a registration module which registers each vehicle. Additionally, a vehicle user may register with the facial skin analysis application to have his/her facial skin analyzed when travelling in any of the plurality of vehicles. The facial skin analysis application is operatively connected to a skin data AI analytics module and data lake and searches a plurality of databases for information related to the facial skin conditions to improve the treatment recommendation.

20 Claims, 12 Drawing Sheets

(52) U.S. Cl.
CPC ............... *G06T 2207/20084* (2013.01); *G06T 2207/30088* (2013.01); *G06T 2207/30252* (2013.01)

(56) References Cited

U.S. PATENT DOCUMENTS

| | | |
|---|---|---|
| 10,130,159 B2 | 11/2018 | Chang |
| 2003/0065578 A1* | 4/2003 | Peyrelevade ........... G06T 11/00 705/26.7 |
| 2003/0065636 A1* | 4/2003 | Peyrelevade ........... G06T 11/00 706/62 |
| 2003/0136600 A1* | 7/2003 | Breed ..................... B60R 22/20 180/272 |
| 2016/0213126 A1* | 7/2016 | Chang ................... A61B 5/0022 |
| 2017/0251925 A1 | 9/2017 | Bouthillier |
| 2017/0296874 A1 | 10/2017 | Zamir et al. |
| 2020/0146622 A1* | 5/2020 | Bock ..................... G06T 7/0016 |
| 2020/0170564 A1* | 6/2020 | Jiang ..................... A61B 5/441 |
| 2021/0027897 A1* | 1/2021 | Rasochova .......... A61B 5/0013 |

* cited by examiner

METHODS AND SYSTEMS FOR IMPROVING HUMAN FACIAL SKIN CONDITIONS BY LEVERAGING VEHICLE CAMERAS AND SKIN DATA AI ANALYTICS

BACKGROUND

Technical Field

The present disclosure is directed to improving human facial skin conditions by leveraging vehicle cameras and skin data artificial intelligence analytics.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The human skin is a large and highly complex organ, consisting of different layers and cell types. It serves as a barrier between the external environment and the inside of the body. The facial skin fulfils a large range of functions, including prevention of percutaneous water loss, temperature maintenance, sensory perception, and immune surveillance. In addition, skin health and appearance play crucial roles for self-esteem and social interactions.

As life expectancy rises, prevention of age-related skin damage has received growing interest. Large monetary sums are spent each year on age prevention treatments of the facial skin. In some professions, a youthful appearance may be a positive factor in promotions and monetary compensation.

Skin undergoes deleterious changes with the passage of time. Some internal factors that affect skin aging are heredity, ethnic origin, dietary variations and hormonal changes. External factors may include environmental factors such as sunlight (UV radiation), humidity, and free radicals. For example, chronic exposure to UV irradiation causes an aged phenotype (photoaging) that is superimposed with aging caused by the passage of time (chronological aging). As a result, areas of the body that are frequently exposed to the sun such as the face, neck, forearms, or back of the hands acquire visible signs of aging more rapidly than other areas of the body. The passage of time and repeated exposure to harmful aspects of the environment alter both the epidermal and dermal compartments of the facial skin. Clinically, chronologically aged skin appears thin, dry, and finely wrinkled. Photoaged skin typically appears leathery, lax, with coarse wrinkles, "broken" appearing blood and uneven pigmentation with brown spots.

Wrinkles are lines or folds which appear on the facial skin. Wrinkles may occur due to the reduction of collagen in the facial skin. Collagen and elastin are the main components of the dermis layer. Loss of these collagen has a negative impact on moisture and elasticity skin which which can cause wrinkles. Wrinkles can be seen clearly in some areas of face, such as forehead, outer corner of the eye, below eyes, cheeks, and between the cheeks and upper lip.

Melanin is a group of natural pigments that add color to hair and skin. Melanin is produced by melanocytes that are confined in the basal layer of the human epidermis and the bulb of hair follicles. Melanin pigments are photoprotective and their production is induced during tanning by ultraviolet (UV) irradiation. As a result, skin pigmentation and reactive tanning after exposure to UV irradiation is reduced with age in sun-protected areas. In chronically sun-exposed areas, pigmentation becomes uneven with age, and mottled pigmentation is a hallmark of photoaged skin. The most common pigmented lesions in photoaged skin include actinic lengitines ("age spots"), ephelides (freckles), and pigmented solar and seborrhoeic keratosis.

Aging also causes a redistribution of fat that results in reduced subcutaneous-to-visceral fat ratio. On sun exposed areas such as the face, aging also causes a redistribution of fat between subcutaneous facial compartments, which is an important part of perceived facial aging. (See: Rittie', L.; Fisher, G., "*Natural and Sun-Induced Aging of Human Skin*", Cold Spring Harb Perspect Med 2015; 5:a015370, incorporated herein by reference in its entirety).

Big data includes information garnered from social media, data from internet-enabled devices (including smart phones and tablets), machine data, video and voice recordings, and the continued preservation and logging of structured and unstructured data. Big data refers to the dynamic, large and disparate volumes of data created by people, tools and machines which are distributed over a set of storages. The data gathered may be stored beforehand or may be a continuous stream to be accessed, stored and analyzed with distributed algorithms and frameworks.

Big data AI analytics is the often complex process of examining large and varied data sets, or big data, to uncover information, such as hidden patterns, unknown correlations, market trends and customer preferences, which can help users make informed decisions. Big data analytics requires a set of distributed computing, networking and storage resources that may be available locally or are rented from a cloud infrastructure. In this manner, big data is related to cloud computing.

The Toyota Big Data Center collects and analyzes data from vehicles equipped with a Data Communication Module (DCM), using a next-generation connected-vehicle framework, which transmits data over cellular networks. The Toyota Big Data Center (TBDC) in the Toyota Smart Center analyzes and processes data collected by the DCM, and uses the data to deploy services under high-level information security and privacy controls. (See "Toyota Accelerates Its Connected Car Technology Initiatives", 2016, https://pressroom.toyota.com/releases/toyota+connected+car+technology+accelerates.htm, and "Toyota's Connected Strategy Briefing", 2016; "Toyota to make "Connected Vehicles" its new standard in Japan, Jun. 26, 2018, https://global.toyota/en/newsroom/corporate/23157821.html, each incorporated herein by reference in its entirety).

Regardless of the fact that aging is a biological process and not a pathological condition, it is correlated with various skin and body pathologies, including degenerative disorders, benign and malignant neoplasms. Monitoring of changes in facial skin condition may provide an avenue for early warning of skin cancers, liver damage, autoimmune disease, and the like.

Accordingly, it is one object of the present disclosure to provide methods and systems for improving human facial skin conditions by monitoring the appearance of the facial skin over time by vehicle cameras and comparing the facial skin images to detect differences. The differences may be compared to facial skin images stored in a data lake to determine facial skin aging, medical conditions, and the like. Recommendations as to skin care products, regimes, skin care professions or referrals to dermatologists or other physicians may be made.

SUMMARY

In the exemplary embodiments, methods, systems and non-transitory computer readable medium having instructions stored therein that, when executed by one or more processor, cause the one or more processors to perform a method for improving facial skin conditions using interior vehicle cameras are described, comprising imaging the facial skin of at least one vehicle seat occupant by at least one vehicle camera each time the vehicle occupant occupies a seat in the vehicle, storing the images of the facial skin with timestamps of the images, comparing each current image with at least one previous image, determining changes between the current image and the at least one previous image, determining a facial skin condition based on the changes, accessing facial skin data which includes facial skin conditions based on at least one of age, gender, ethnic origins and medical diseases affecting the facial skin, accessing treatment options for the facial skin conditions, accessing facial skin care product information, determining a facial skin treatment recommendation based on the changes, the facial skin data, the treatment options and skin product information, and notifying the vehicle seat occupant of the facial skin changes and the facial skin treatment recommendation.

In another embodiment, the facial skin analysis is performed by a CPU of the vehicle and/or a CPU in a data center.

In another embodiment, the facial skin analysis is performed by the CPU of the vehicle to determine a skin condition and a facial skin analysis application is accessed to search a data lake using skin data artificial intelligence analytics to improve the treatment recommendation.

In an additional embodiment, skin condition information and treatment recommendations are gathered by a plurality of vehicles and stored in a database of a data lake.

In an embodiment, a vehicle user may register with a facial skin analysis application. When the vehicle user enters a vehicle connected to the facial skin analysis application, the vehicle camera images the facial skin of the vehicle user and sends the images to the facial skin analysis application. A vehicle user profile may be stored entirely within the facial skin analysis application with previous facial skin images of the vehicle user. The facial skin analysis application may determine a skin condition by comparing the current facial skin images with the previous facial skin images of the vehicle user. The facial skin analysis application may access facial skin data AI analytics and search a data lake for information related to the facial skin condition. The facial skin analysis application may correlate the information with the facial skin condition and user profile, and make a treatment recommendation for the facial skin condition. The facial skin analysis application performs computations, performs skin analysis and provides the treatment recommendation to the vehicle user.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
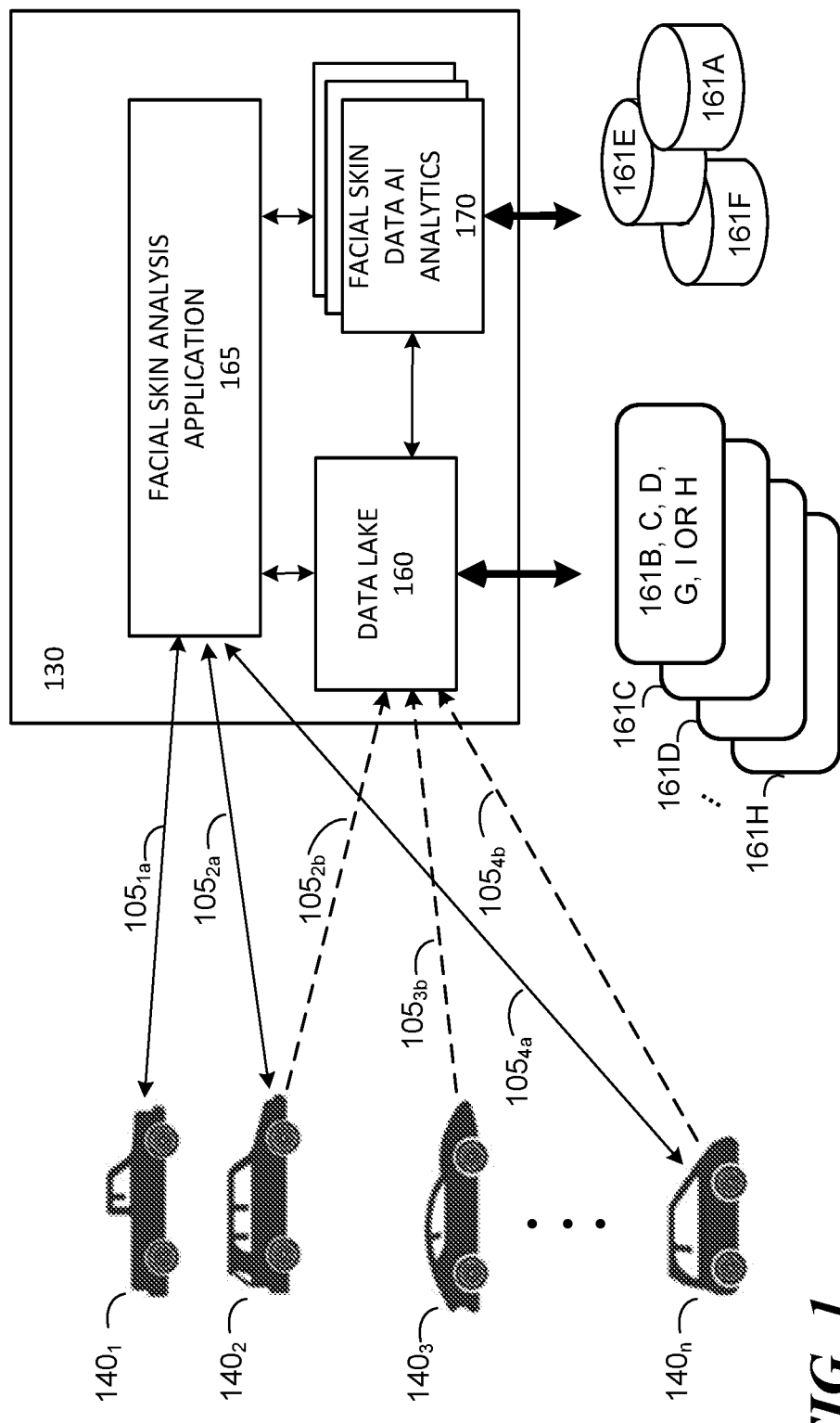
FIG. 1 is an illustration of the facial skin analysis system, according to certain embodiments.

In the drawings, like reference numerals designate identical or corresponding parts throughout the several views. Further, as used herein, the words "a," "an" and the like generally carry a meaning of "one or more," unless stated otherwise. The drawings are generally drawn to scale unless specified otherwise or illustrating schematic structures or flowcharts.

Furthermore, the terms "approximately," "approximate," "about," and similar terms generally refer to ranges that include the identified value within a margin of 20%, 10%, or preferably 5%, and any values therebetween.

Aspects of this disclosure are directed to a method for improving facial skin conditions using interior vehicle cameras, a system for improving facial skin conditions using interior vehicle cameras and non-transitory computer readable medium having instructions stored therein that, when executed by one or more processors, causes the one or more processors to perform a method for improving facial skin conditions using interior vehicle cameras.

After a certain age, for example, the age of 20 years, the perception of a person's age may become a factor affecting self-esteem and earnings capacity. A person's age can be determined by facial characteristics, such as wrinkles, age spots, blemishes, sagging skin, deep shadows or the like.

Another skin care concern is that facial skin changes, such as in color, pigmentation, and topology may indicate medical conditions and provide early warning of illness.

Although skin care should be a primary concern based on its impact on perceived age and earnings capacity, many people look in a mirror for only 10 to 20 minutes per day to view or take care of their facial skin.

The mechanisms for helping a person improve his/her skin and prevent the facial skin from aging, pre-mature aging, other facial skin conditions and providing early warning of disease, such as skin cancer, and heart or liver problems based on the facial skin conditions, has conventionally meant a physical visit to a physician, dermatologist, cosmetologist or health care professional. Skin lotions and cosmetics have been used to improve the facial skin or cover the signs of aging. Detection of changes in the facial skin has conventionally been determined by a dermatologist by visual inspection of a limited range of images. A dermatologist may take photographs of the facial skin and compare the images over time for a limited number of visits. A video of the facial skin may be used to identify skin changes, such as wrinkles or pigmentation changes with a set time period, i.e., the period of time in which the video is recorded. However, a daily or hourly inspection of the facial skin over weeks, months and years has not previously been utilized to identify skin changes and/or medical conditions.

The internal camera(s) of a vehicle can be configured to capture human face and skin images at regular intervals (such as several times per day, over weeks, months and years or every time the human enters the vehicle). Comparisons of these images may be able to provide skin and aging analysis superior to those captured in a dermatology office, since the vehicle images may represent a long and extensive history of the face and skin of the driver and passengers. Aspects of the present disclosure may utilize data center applications and search a data lake with artificial intelligence analytics mechanisms and perform skin related condition analyses based on these vehicle images.

A data lake is a centralized repository that stores structured and unstructured data of large scale. Big data analytics may search the data lake with queries to find information related to the queries and train artificial intelligence machine learning programs to detect patterns in the information.

Big data collected by vehicle cameras can include millions and possibly billions of skin images of all skin types, colors, ages, genders, etc. The facial skin data collected by the vehicle cameras may be stored in the data lake of the data center. Medical data related to facial skin conditions and information on recommended treatment are also stored in the data lake or accessed by the data lake or the facial skin data AI analytics modules. Additionally, the data lake may link to or include structured data sourced from data warehouses. Based on this data, the facial skin analysis system can correlate the facial skin images with the medical data and determine a facial skin condition. The facial skin analysis system further can access medical databases of physicians, dermatologists and health care professionals and may recommend a physician, dermatologist or health care professional near the home or current location of the driver or passenger. The facial skin analysis system can also store information related to cosmetologists, skin regimes, stress therapy, cosmetics and lotions and recommend a non-medical treatment based on the facial skin condition.

In a further aspect of the present disclosure, the facial skin analysis application stores data from a plurality of vehicle users in the data lake. The skin data in this population is used to analyze and recommend treatments to vehicle users.

In an aspect of the present disclosure, the facial skin analysis system may be a subscription based application and/or may be included with the vehicle. In either case, the identities of the driver and passengers are protected by strict high-level information security and privacy control.

Whether subscription based or a vehicle program, the drivers of the vehicle may be identified by facial recognition or by other sensors, such as weight sensors or fingerprint readers. The fingerprint readers may be located on the steering wheel or may be in another location near the interior dashboard or on a user interface. A passenger may further be identified by a vehicle camera or by fingerprint readers. The identification of the driver or passengers is not limited to camera images or fingerprint readers. The identification may also be made by any of retinal readers, voice recognition, weight sensors or the like.

The methods of the present disclosure include leveraging artificial intelligence (AI) and analytics technology, to provide baselines for each skin type.

In a non-limiting example, a camera image of the face of a driver of a vehicle is applied to an in-vehicle skin analysis system. The facial skin analysis system detects a change in his/her facial skin condition, such as wrinkles or stress lines indicating rapid aging based on images collected over a time period, for example, over the last three month period. The vehicle system may send a notification alert to the driver, such as: "your skin indicates you have aged 2 to 3 years within the past 3 months", "your skin tone is paler and there are more wrinkles on your forehead", "Possible causes are stress or dryness. Check with your primary doctor and dermatologist". The system may recommend health care professionals or health products related to the appearance of rapid aging. The facial skin analysis system may be a standalone system in which the processing is performed by the vehicle computing system. The facial skin analysis system may access the recommendations within the vehicle memory or may connect to a facial skin analysis application stored in a data center, which is operatively connected to skin data AI analytics and a data lake to search for information related to the facial skin condition. The facial skin analysis application may correlate the information with skin condition and make treatment recommendations which are transmitted back to the driver. Further, the facial skin analysis application may update the memory of the vehicle with the treatment recommendations.

In another non-limiting example, a camera image of the face of a driver of a vehicle may be transmitted to a facial skin analysis application and stored in a data center in a data lake. The facial skin analysis application detects a change in his/her facial skin condition in which the facial skin appears to have a greater number of dark spots based on images collected over the last year. The facial skin analysis application accesses big data artificial intelligence analytics and searches for information from the data lake to determine skin treatments for the dark spots. The facial skin analysis application may suggest lotions, products, a skin care regime or concealing make-up. Additionally, the facial skin analysis system may suggest that the driver should visit a cosmetologist, dermatologist or other skin care professional. The application may recommend cosmetics, skin lotions, make-up, a health care professional, a cosmetologist, dermatologist or other skin care professional based on the analysis of the dark spots.

In a further non-limiting example, camera images of the face of a driver are applied to an in-vehicle skin analysis system. The vehicle may further include sensors on the steering wheel which measure the driver's heart rate. Images indicating changes in skin color or skin blotching may be correlated to the driver's heart rate and a health score may be determined. An alert may be sent to the driver to pull over and an ambulance may be called by the vehicle system if the health score is dangerously high.

In another non-limiting example, camera images of the face of the driver may show an increase in color. The vehicle may instruct the driver to breathe into a breathalyzer and analyze the breath to determine whether the blood alcohol is over a legal limit. The vehicle may instruct the driver to allow another seat occupant to drive or may lock the ignition until a further breathalyzer test indicates that his blood alcohol levels have decreased below legal limits.

Aspects of the present disclosure may use big data sources to obtain current and historical and/or predictive information to form a facial skin analysis database.

For example, the current and historical information may be sourced from the data lake which is compiled from raw or uncorrelated images of the facial skin of other drivers connected to the facial skin analysis system. The data lake or a (separate or additional) facial skin database may further include skin images which have previously been correlated to facial skin conditions, such as from medical databases. In a non-limiting example, some databases from which skin images or correlations may be accessed are the "HAM10000 Dataset" (also known as the "Kaggle Dataset") which is a large collection of multi-source dermatoscopic images of pigmented lesions, (See: https://www.kaggle.com/kmader/skin-cancer-mnist-ham10000), the "Dermatologist Disease Database", (See: https://www.aocd.org/page/DiseaseDatabaseHome), and dermatology datasets accessed from sources such as universities.

Cloud computing is network-based computing in which typically large collections of servers housed in data centers or "server farms" provide computational resources and data storage as needed to remote end users. Some cloud computing services provide access to software applications such as word processors and other commonly used applications to end users who interface with the applications through web browsers or other client-side software.

An application execution system that executes online web applications can implement a platform for distributing web applications. The web applications can be developed on the application execution system and distributed through an online store. Distributed web applications can be installed on accounts so that user data of users that access the installed web application can be segregated from access by developers of the web application, and source code of the web application can be segregated from access by users or purchasers of the web application.

A software application is deployed on a computing platform, by a data center, which may be a proprietary data center. The computing platform includes access to storage systems, databases, analytics programs, as needed, that can provide functionality that is required by the application.

An overview of the system for improving human skin aging is shown in FIG. 1. Vehicles $140_1$, $140_2$, $140_3$, $140_4$ each include an onboard communication system which is configured to communicate with data center 130. Each vehicle may communicate with the facial skin analysis application 165 stored in the data center 130 over communication channels $105_{1a}$, $105_{2a}$, etc. Skin images and/or initial skin analysis by the vehicle may also be communicated over communications channels $105_{2b}$, $105_{3b}$, etc. for storage in the data lake 160, independently or at the same time as the communication to the facial skin analysis application 165.

The facial skin analysis application 165 is stored in the data center 130 and may access the data lake 160 and the skin data artificial intelligence (AI) analytics program(s) 170 in performing the facial skin analysis. The skin data AI analytics module(s) 170 may include more than one type of analytics program. The data lake 160 collects raw data (unprocessed or uncorrelated) from a plurality of vehicles 140 and may also include or link to a plurality of more organized databases which contain skin data ranked, prioritized, organized and correlated to skin conditions, age, ethnic groups, skin color, skin textures, skin diseases, medical conditions affecting the skin, etc. which are extracted, transformed, processed, loaded into the data analytics.

Within the skin data analytics, where skin data is more refined, the data is further processed with complex algorithms and machine learning to provide best analysis results to the facial skin analysis application.

Figure 2A:
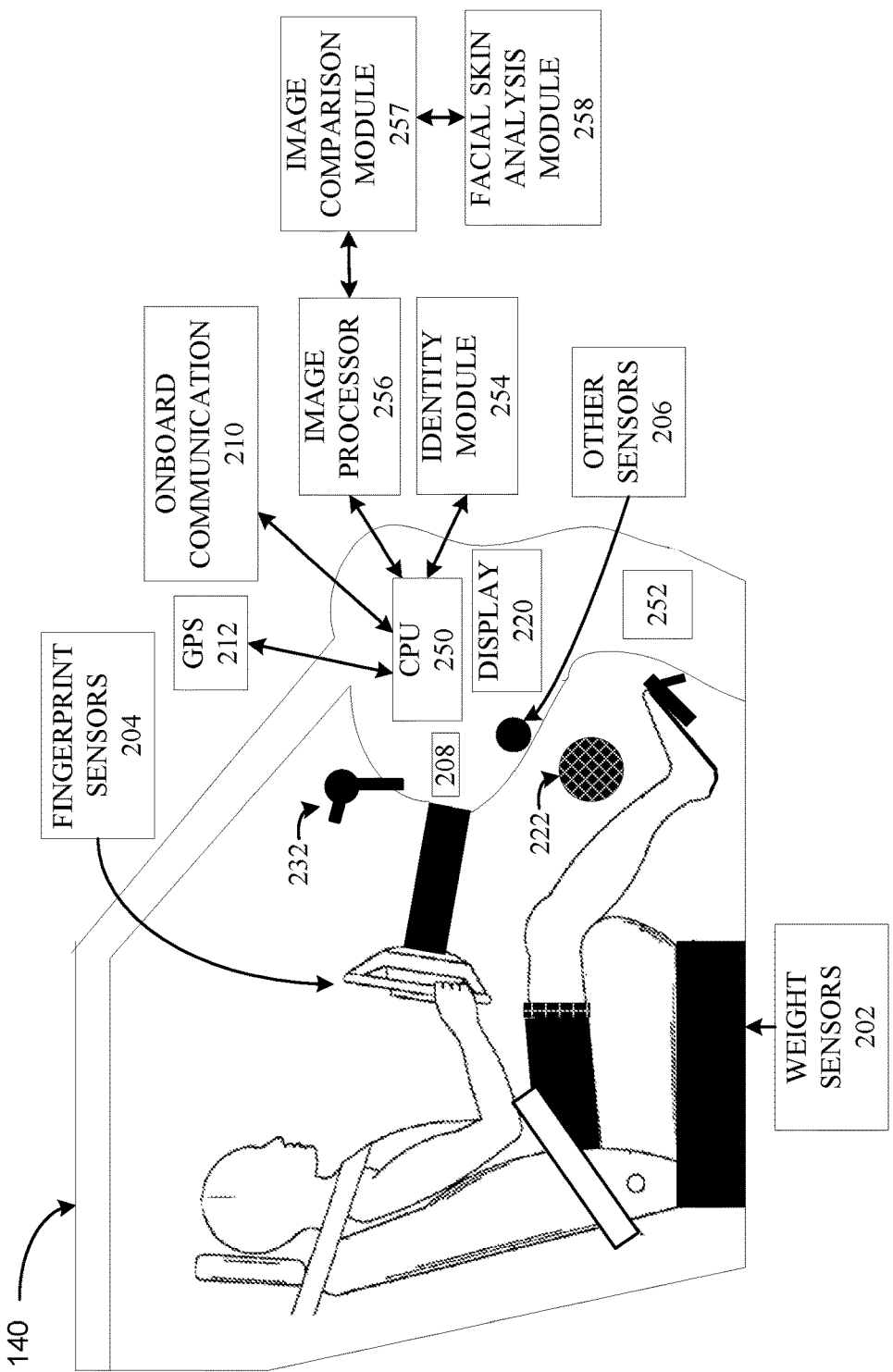
FIG. 2A illustrates a vehicle having an onboard communication module and skin analysis capability, according to certain embodiments.

As shown in FIG. 2A, vehicle 140 includes a control system including a CPU 250, one or more sensors (202, 204, 206), an onboard communication module 210, a GPS unit 212, a display 220, an image processor 256, an image comparison unit 257, skin analysis module 258, memory 252, and one or more cameras 232. A camera 232 may be directed to the face of the driver or toward the face of a passenger to record images. The vehicle may have multiple cameras ($232_1$-$232_n$, FIG. 2B)) directed to driver or passenger facial locations. These images and their timestamps are sent to the CPU 250, which includes circuitry for processing the images by image processor 256, storing the images in memory 252, comparing the images over time via image comparison module 257 and determining a facial skin condition by facial skin analysis module 258 based on a series of images. The CPU 250 may further identify the driver or passenger by the images via identity module 254 and may store the images in a database in memory 252, which includes profiles of the driver or passenger(s). Additionally, the CPU 250 may be configured to use the images with data obtained from the other vehicle sensor(s), such as fingerprint sensors 204 on the steering wheel, weight sensors 202, other sensors 206, such as audio sensors, heart rate sensors or the like, or inputs at a user interface 208 to determine the identity of the occupant of the vehicle.

Figure 2B:
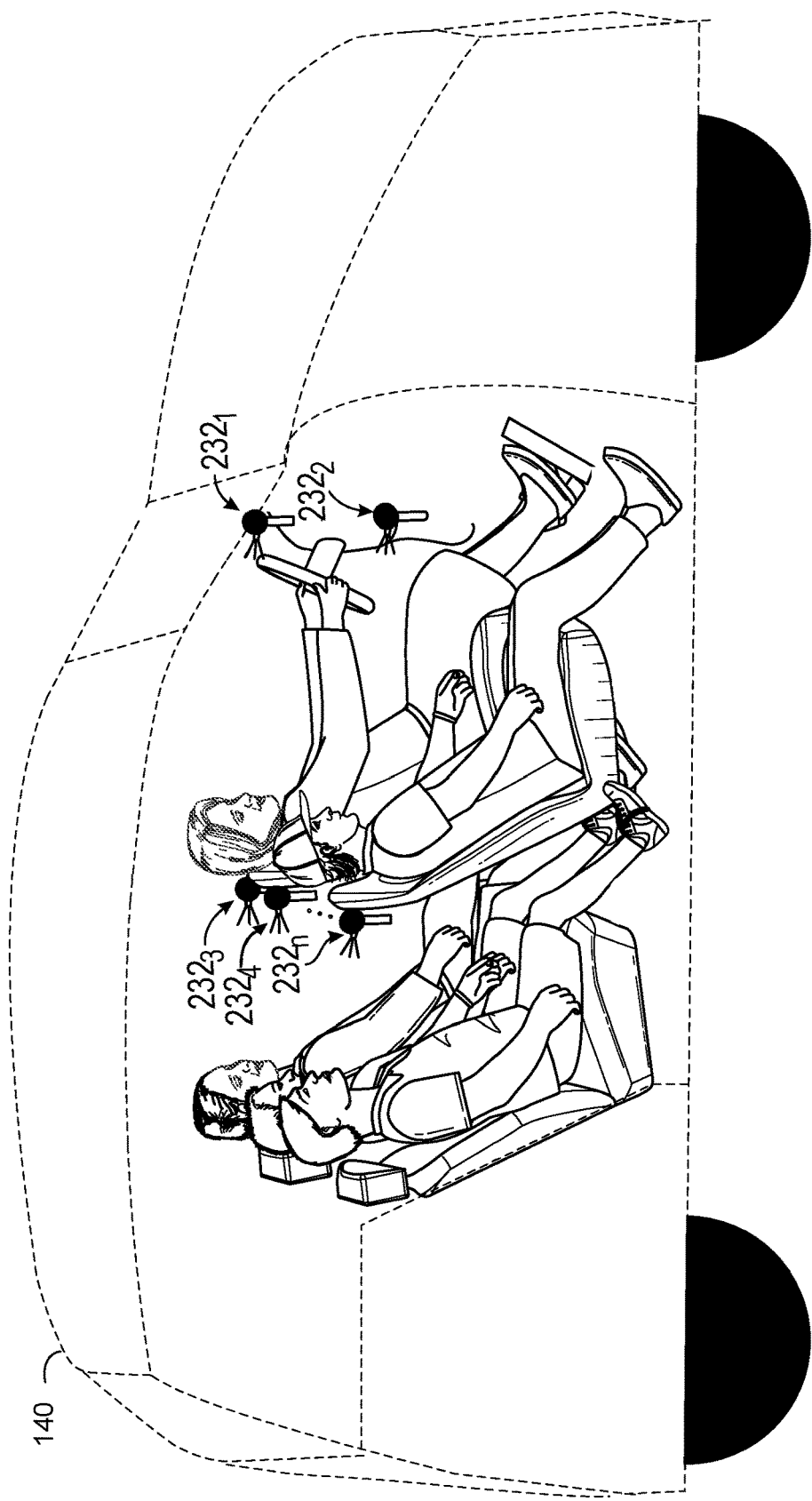
FIG. 2B illustrates cameras arranged to image seat occupants, according to certain embodiments.

Referring to FIG. 2B, the vehicle 140 may include a plurality of cameras ($232_1$, $232_2$, $232_3$, $232_i$) each directed at the level of a face of a person seated in each different seat position. The cameras at the front of the vehicle may be mounted on the dashboard or rear view mirror of the vehicle. The cameras pointing toward the passengers in the back of the vehicle may be mounted on the seat backs or in the ceiling or support structures of the vehicle. The positions of the cameras are not limiting and the cameras may be any type of camera and may be placed in any location which allows a field of view including the occupant's face.

As shown in FIG. 2A, weight sensors 202 beneath or within each seat may indicate whether the seat is occupied and the weight of the occupant. The CPU 250 includes circuitry configured to adjust the focus and direction of the camera lens based on the weight of the occupant, which may indicate the height of the occupant. For example, a weight of 55 pounds may indicate a child of about 7 years. A range of average heights stored in memory 252 may be correlated to the weight to allow the camera to focus on a face. Alternatively, the weight and height of each occupant may be stored at the time of registration and used to redirect the camera's field of view. The height may be adjusted over time by the identify module if the vehicle occupant is a child.

Alternatively, the identity module may request the input of a voice of the passenger, a breath may be required at a breathalyzer, a fingerprint may be requested at the user interface 208, or the like, to generate an identification of the seat occupant.

The image processor receives the images of the identified driver or passenger and stores the images and memory in a database in memory 252. Memory and/or database may store user profiles of drivers and passengers of the vehicle, and historical facial skin images of each driver and passenger.

The images of each driver and/or passenger are stored over time, such as days, weeks, months and years. These images are compared by image comparison module 257 to determine changes in the images over time. The time period of comparison is preferably in the range of one hour to five years, more preferably in the range of one hour to one year, most preferably in the range of one hour to two months. The vehicle includes a facial skin analysis module 258, which determines a facial skin condition, such as color, wrinkles, stress lines, dark spots, protrusions, moles, and the like from the changes in the images.

The facial skin analysis module may provide audio or display feedback directly to the identified driver or passenger, such as "Your face is showing signs of stress. Would you like to hear soothing music?" or "You have developed wrinkles on your forehead in the last six months. Lotion XXX has been shown to be effective in reducing wrinkles".

Figure 3A:
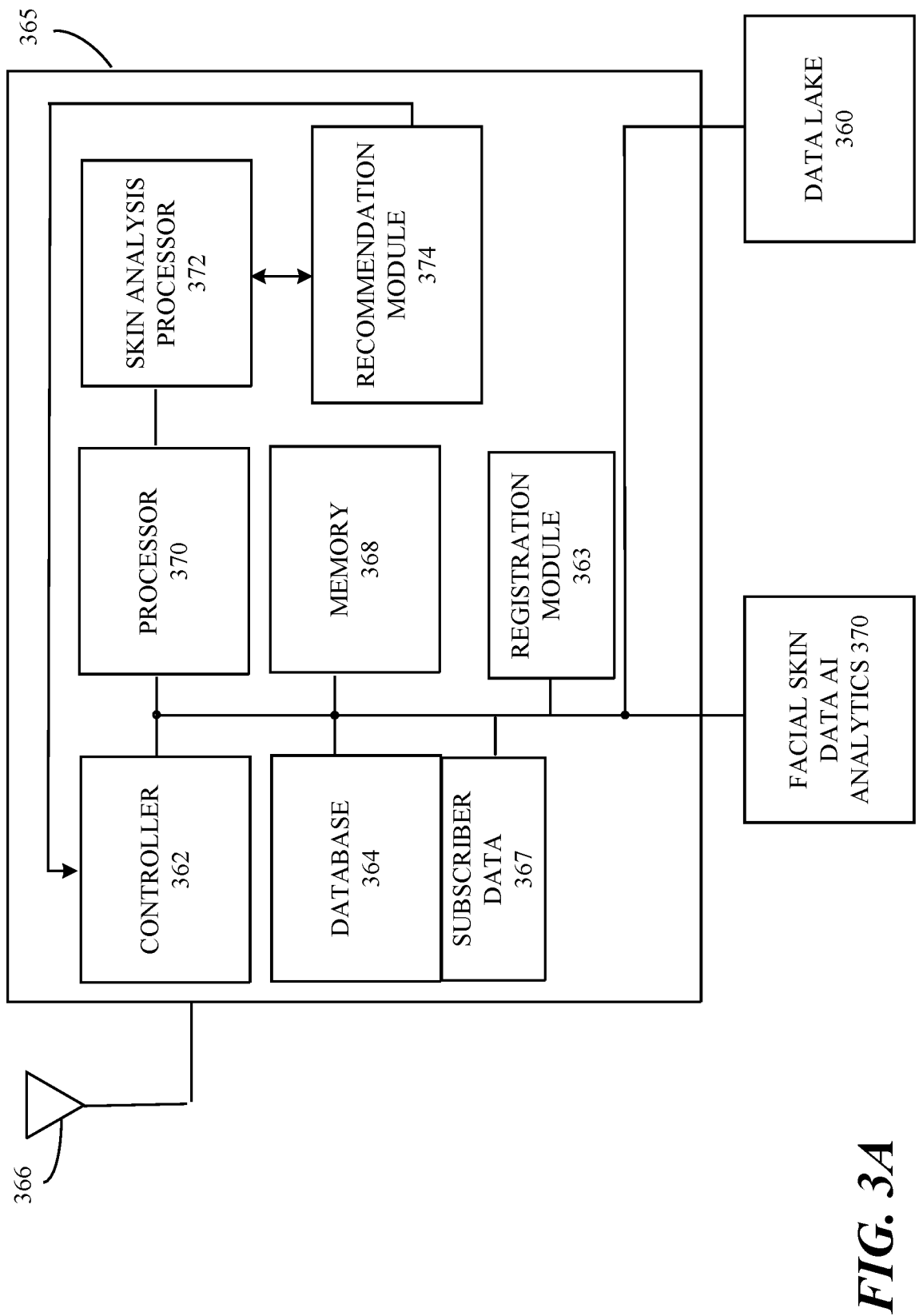
FIG. 3A depicts the computing system of the facial skin analysis application, according to certain embodiments.

Alternatively, the facial skin analysis module may recommend medical treatment when skin disease appears to be indicated. In a non-limiting example, the feedback provided may be "The boundaries of your facial mole on the upper right quadrant of your forehead have changed dimensions in the last two months. It is recommended that you visit your dermatologist to have this mole examined". If a user profile contains the names and telephone numbers of the dermatologist of the identified driver or passenger, the facial skin analysis module 258 may ask if the driver or passenger would like to call the dermatologist, and the onboard communication module may process the call. Alternatively, the facial skin analysis module may recommend a dermatologist from a stored list of medical professionals in the home location of the identified driver or passenger. The facial skin analysis module 258 may work in conjunction with facial skin analysis application 365, which is able to provide more extensive skin analysis through accessing the data lake 360 and trained AI search and analytics program(s) 370 as shown in FIG. 3A.

Within the vehicle 140, the CPU 250 is implemented, for example, using one or more ECUs. In particular, the CPU 250 is communicatively coupled to the one or more sensors (202, 204, 206), display 220, image processor 256, an image comparison unit 257, facial skin analysis module 258, memory 252, and one or more cameras 232 to receive data therefrom, for example, via a transmission or signal wire, a bus (e.g., a vehicle CAN), radio frequency, etc. Further, the CPU 250 is communicatively coupled to the onboard communication module 210 to transmit and receive communications to or from the facial skin analysis application 165 in the data center 130.

The CPU 250 may comprise a single central processing unit (CPU), or could comprise two or more processing units. For example, the processing unit 250 may include general purpose microprocessors, instruction set processors and/or related chips sets and/or special purpose microprocessors such as application specific integrated circuits (ASICs). The processing unit 250 may also comprise a memory or storage for caching and other purposes. Those of ordinary skill in the art understand that any other node, controller, unit, database and/or device described herein may be similarly implemented.

Principal components of a CPU include an arithmetic logic unit (ALU) that performs arithmetic and logic operations, processor registers that supply operands to the ALU and store the results of ALU operations, and a control unit that orchestrates the fetching (from memory) and execution of instructions by directing the coordinated operations of the ALU, registers and other components.

The memory 252 is a computer readable medium and is connected to the CPU 250. The memory stores computer readable instructions e.g. in the form of computer program modules. For example, the memory 260 may be a flash memory, a Random-Access Memory (RAM), a Read-Only Memory (ROM) or an Electrically Erasable Programmable ROM (EEPROM).

The facial skin analysis module 258 may access a database in memory 252 when determining facial skin conditions. The facial skin conditions are transmitted by onboard communications module 210 to facial skin analysis application 165 in data center 130 for further analysis. The facial skin analysis application may alternatively be implemented in any one of a cloud computing environment, a web application residing on one or more servers, a website, a block chain system and a distributed server system accessible by data center 130.

Within the data center 130, the facial skin analysis application 165 has access to a data lake 160 and to facial skin data artificial intelligence (AI) programs 170. The facial skin data AI analytics uses algorithms to find subtle relationships in a large set of "training" data, such as image data or facial skin condition data received from connected vehicles 140 (a vehicle having an onboard communications system which is capable of transceiving over LTE is known as a "connected vehicle"). The training process locates those relationships and encodes them into a "model," such as a neural network. The model can then be used to find relationships between inputs similar to those in the training data. The trained model itself may reside anywhere it can receive inputs and provide outputs.

As shown in FIG. 3A, the facial skin analysis application (165, 365, FIG. 1, 3A) may include a controller 362, at least one database 364 including subscriber data, at least one transceiver 366, at least one memory 368 including program instructions, a processor 370 operatively connected to skin analysis processor 372 which is configured to use the program instructions to process facial skin conditions and facial skin images received from the onboard communications module 210 of a connected vehicle 140, request a search of a data lake 360 of similar facial skin conditions, perform analyses of the search results by facial skin data AI analytics 370. Skin data AI analytics 370 may be configured to prepare search queries for searching the data lake for the causes and treatments for the facial skin conditions and correlate the results of the search with the skin data of a particular vehicle occupant. The data lake may further store the information regarding treatment for facial skin conditions. In a non-limiting example, the data lake may store the names of dermatologists in the home area of the identified driver or passenger. In a further non-limiting example, the data lake may store the names of dermatologists, cosmetologists or medical professionals in the current location of the connected vehicle 140 based on GPS data received from the vehicle. In another non-limiting example, the data lake may store lists of skin repair products recommended for a facial skin condition of the identified driver or passenger, and provide the names of retail outlets in the current or home location which carry the products.

The database 364 can represent one or more local and/or external databases and/or memory 368 communicably coupled to the controller 362. A subscriber database 367 can store a user profile including historical facial skin images or facial skin condition analyses, physicians, dermatologists, cosmetologists and preferred retail outlets of the identified driver or passenger.

The data center 130 can represent one or more servers communicably coupled to the on-board communication module 210. For example, a server may include processing circuitry configured to operate the system 100, receive data from the onboard communication module 210, receive statistical information from the database 364 or subscriber database 367, and the like. The data center may include an application server which hosts a web application which performs some or all of the processes of the facial skin analysis service. The server may include a communication endpoint or find other endpoints and communicate with those endpoints. The data center may share computing resources, such as CPU and random-access memory over a network. A server may be a virtual server or a web server. The data center is connected to a communications network which enables the communication between the on-board communication module, satellites or base stations and at least one connected vehicle 140.

The processing circuitry of the facial skin analysis application 365 residing in the data center 130 can carry out instructions to perform or cause performance of various functions, operations, steps or processes of the system 100. The controller 362 and processing circuitry 370 can be configured to store information in memory, operate the system 100, and receive and send information in the form of signals between the sensors (202, 204, 206, 208), the camera(s) 232, the CPU 250, the controller 362, the facial skin data analytics programs 170 and the data lake 360. The facial skin analysis processor 372 may compile the facial skin analysis information and a recommendation as to a treatment for the facial skin condition may be made by recommendation module 374. The recommendation is fed back to the controller 362, which transmits the recommendation to the CPU 250 of the vehicle 140. The CPU 250 provides the recommendation as feedback to the occupant. If the occupant has downloaded the facial skin analysis application 365 to a person computing device, such as a tablet, smart phone or personal computer, the facial skin analysis application may communicate the recommendation back to the occupant by email, messaging, or the like.

The data center 130 may be connected to the onboard communication module 210 through a network. The network can be a public network, such as the Internet, or a private network such as a local area network (LAN) or a wide area network (WAN) network, or any combination thereof and can also include a public switched telephone network (PSTN) or integrated services for digital network (ISDN) sub-networks. The network may wireless such as a cellular network including EDGE, 3G, 4G, 5G and LTE/LTE-A wireless cellular systems. The wireless network can also be Wi-Fi, Bluetooth, or any other wireless form of communication that as is conventionally known.

The controller 362 receives data communications from the on-board communication module 210 of the vehicle 104. The controller 362 also receives GPS data 212, data entered at graphical user interface 208, search results from data lake 360 and/or skin data AI analytics 370. The controller 362 may send a request to the skin data AI analytics 370 to search the data lake 360 and other databases and data warehouses for historical and/or predictive information relevant to the type of facial skin condition. In a non-limiting example, the facial skin data AI analytics module may search the data lake with search tools, such as Elastic Search, Azure Data Explorer and Talend, Based on the query, the data lake may return information regarding skin diseases, facial aging, causes and treatments related to the facial skin condition. The data lake, databases and data warehouses may also provide product listings, preferred lists of medical professionals, skin care professionals, and the like.

Figure 3B:
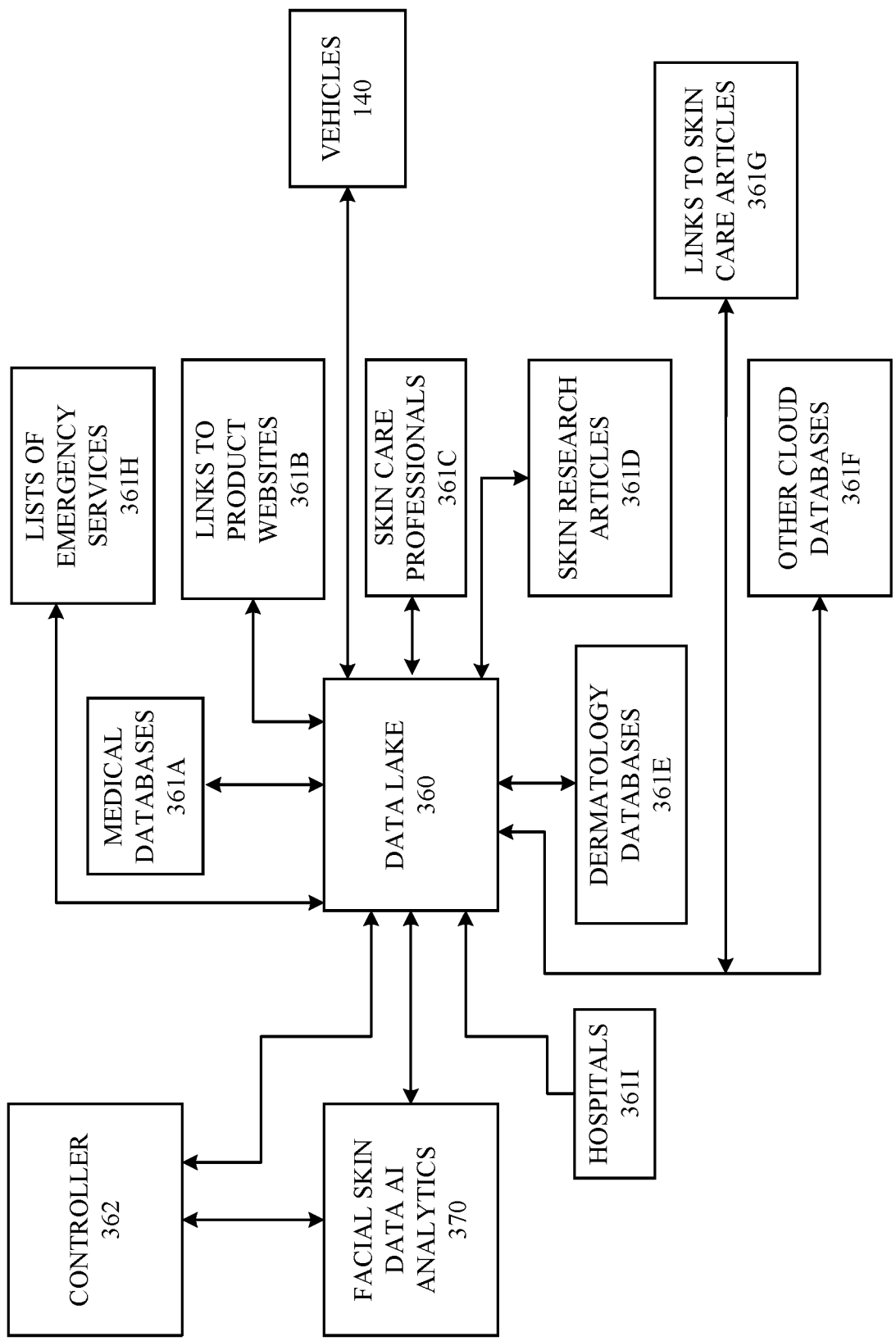
FIG. 3B is a block diagram of the facial skin data AI analytics and the data lake connected to the facial skin analysis application, according to certain embodiments.

FIG. 3B depicts how the data lake 360 and skin data analytics 370 are implemented in the data center 130. The data lake 360 stores the records of all the images and facial skin conditions sourced from the connected vehicles 140, along with recommendations made. The data lake is also connected to a plurality of cloud storage databases, such as medical databases 361A, skin care professional databases 361C, and dermatology databases 361E. The data lake additionally links to product websites 361B, skin research articles 361D, skin care articles 361G, and other databases 361F or relevant links, which may be websites, news articles, social media, or the like. The data lake may also link to lists of emergency services in the current location of the connected vehicle, which may be accessed, for example, if the facial skin analysis indicates a flushed appearance or bright facial spotting over a short time period in conjunction with increased heart rate as sensed by a vehicle heart rate sensor.

Facial skin data AI analytics 370 analyzes the facial skin images and facial skin conditions received from the connected vehicle 140 and creates search queries, which are applied to the data lake 360. The data lake retrieves the requested information and transmits the information back to the controller 362 and/or to the skin data analytics program(s) 370 for use in skin analysis processing. The data lake may store facial skin data retrieved by the search queries with the records of the images and facial skin conditions, along with treatments and recommendations made for the facial skin conditions. The data lake may store facial skin data from any of the plurality of occupants of vehicles 140. For example, the data lake may store records from millions of vehicles connected to the facial skin analysis application, and the skin data AI analytics may be trained to search, correlate and find patterns in these records related to the vehicle seat occupant's facial skin images and skin condition.

Figure 4:
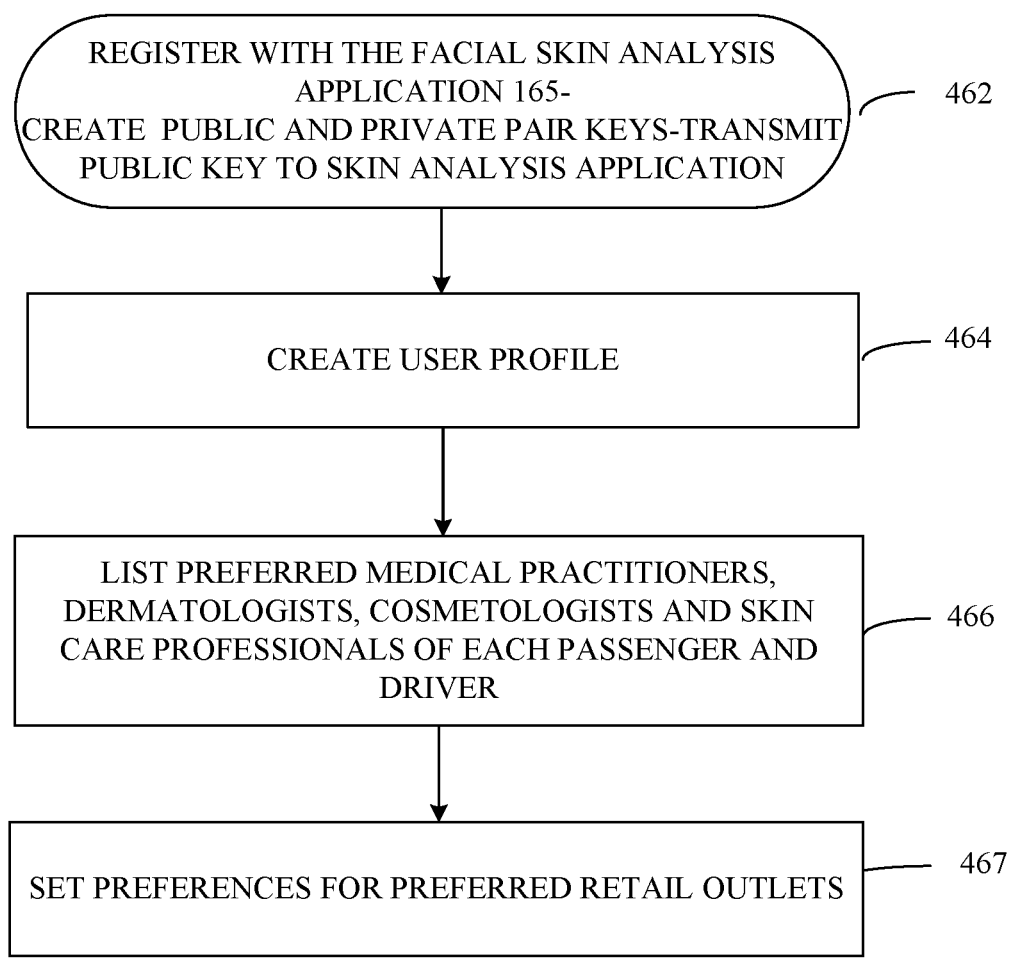
FIG. 4 is an exemplary flowchart of the facial skin analysis application registration process, according to certain embodiments.

FIG. 4 describes the process of registering a user with the facial skin analysis application 165. Registration 462 may entail downloading the facial skin analysis application to a smart computing device of a vehicle user or to the CPU 210 through the onboard communication module 210. Registration comprises the creation of public and private pair keys by the user, and transmitting the public key to the facial skin analysis application. Registration may be for a single user or for a family or group of users. In a non-limiting example, the owner of a connected vehicle may register his/her family with the facial skin analysis application and set up user profiles for each family member. In a second non-limiting example, a company may offer the facial skin analysis application to a group of employees in a wellness program. In another non-limiting example, a ride share company may offer the facial skin analysis application to clients as an incentive for choosing their ride share vehicles.

Registration 462 with the facial skin analysis application 165 may be free or may require a subscriber fee. The facial skin analysis module 258 may be provided with a new vehicle or may be part of an upgrade purchase. Skin analysis module 258 in the vehicle may be updated by connection with facial skin analysis application 165.

Each user, such as the owner, driver or a passenger, may create a user profile 464. The user profile may be for a single user, a family or a group of users. The user profile may include the name of the user, age, height, weight, ethnic origins, address, credit card information and known medical or facial skin conditions. The user profile may include a fingerprint. A fingerprint may be obtained by a fingerprint reader on the steering wheel or at the user interface 208. The user profile may include an image of the user taken at the time of registration by a vehicle camera or uploaded from a computer or smart device of the user.

A list of preferred medical practitioners, dermatologists, cosmetologists and facial skin care professionals of each user is stored at step 466. Additionally, preferences for preferred retail outlets are set. The facial skin analysis application 165 may search the marketplace websites of the preferred retail outlets for recommended skin lotions and notify the user of the availability of a skin care product and compare pricing. The facial skin analysis application may ask the user if he/she wishes to purchase the product and perform the purchase for the user.

An additional method for monetization of the facial skin analysis computer application includes providing sponsored content to a user of the computer application. The sponsored content is provided for use with the facial skin analysis computer application. A provider of the computer application may be compensated in connection with provisioning the sponsored content for use with the computer application. For example, the facial skin analysis application may link the user to preferred medical practitioners, skin care professionals or to websites of recommended skin care products who have signed a contractual agreement with the provider of the facial skin analysis application. The medical practitioners, skin care professionals or websites of recommended skin care products must register with the facial skin analysis application and pay a fee to be placed on the recommended lists. The present disclosure is not limited to the websites and databases 361A-361I listed above and shown in FIG. 3B, which are only a few exemplary instances.

Figure 5:
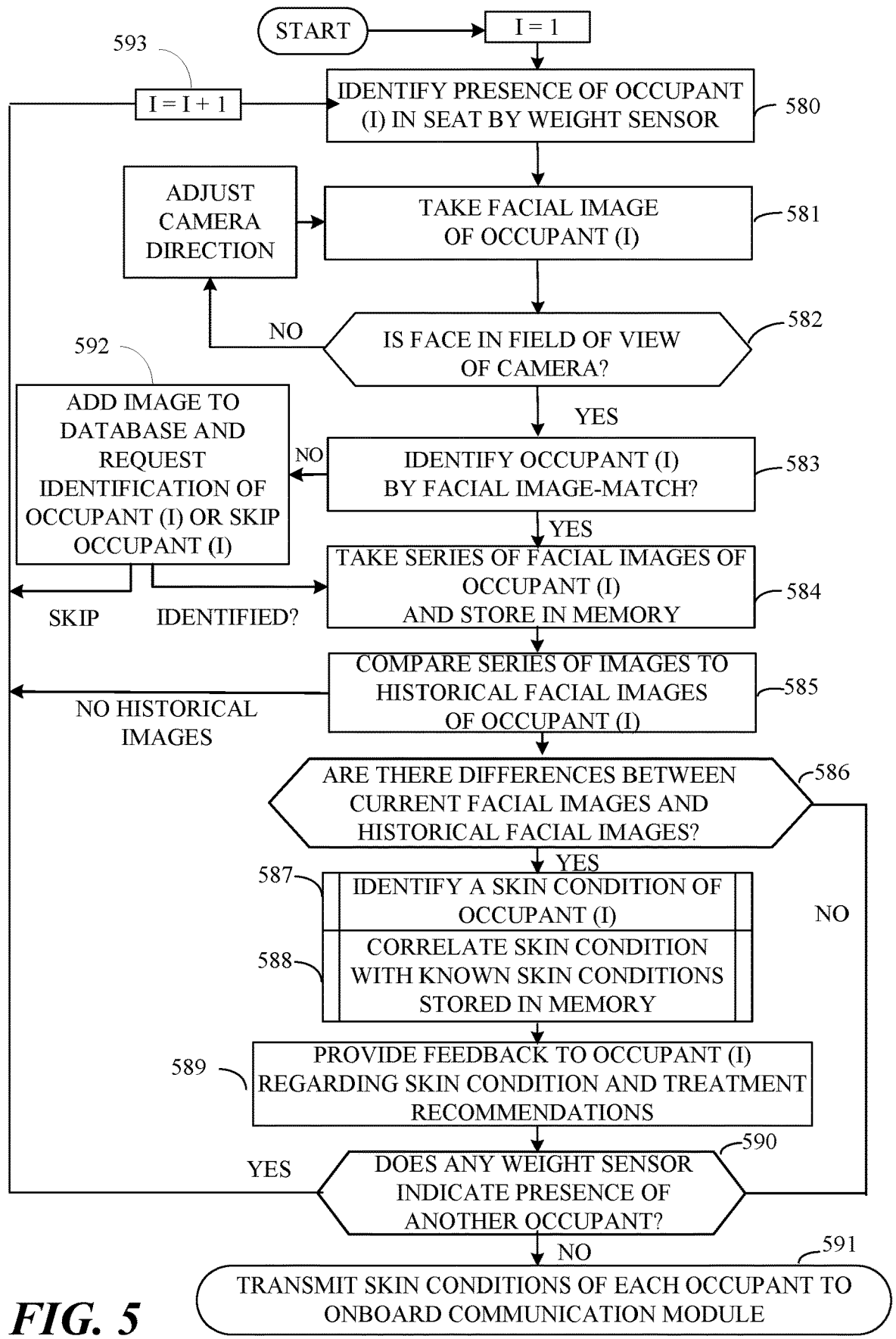
FIG. 5 is an exemplary flowchart of a process for identifying a facial skin condition at vehicle as illustrated in FIG. 2A, 2B using one or more in-vehicle cameras, according to certain embodiments.

FIG. 5 illustrates a process for identifying a facial skin condition at vehicle 140 as illustrated in FIG. 2 using one or more in-vehicle cameras ($232_1$, $232_2$, $232_3$, ..., $232_i$) which can be focused towards the face of a seat occupant as shown in FIG. 4.

To start the facial skin analysis, the presence of a first occupant (I=1, where I=1 to N vehicle occupants) of the vehicle (driver or passengers) is determined by vehicle sensors, such as weight sensors, at step 580. At step 581, the camera takes a facial image of the occupant. At step 582, if the face is not in the field of view of the camera, the camera direction is adjusted and the image is retaken. The image is processed by the image processor 256 and compared to stored profile images which identify registered occupants of the vehicle. If a match is not found, the image is added to the database in memory 252 and the CPU requests through the user interface display or through audio that the seat occupant (I) provide identifying information at step 583. The driver or the occupant may tell the facial skin analysis module to skip occupant (I) if he/she is not a person of interest. For example, a driver giving a ride to a friend or a child's playmate may not wish to add the occupant (I) to the database.

At step 584, a series of facial skin images of occupant (I) are then acquired and stored in memory 252. At step 585, the series of facial skin images are compared to historical facial skin images of the occupant (I). If there are no historical facial skin images for the occupant (I), the process returns to step 593, where (I) is incremented by 1.

At step 586, the process determines whether there are changes between the historical facial skin images and current facial skin images. If NO, then the process moves to step 590 to determine whether the sensors detect another occupant. If further occupants are detected, then the occupant number is incremented and if no further occupants are detected, the facial skin condition of each occupant is stored in memory and also transmitted to the onboard communication module for further analysis of the causes and treatments by the facial skin analysis application.

At step 586, if there are changes between the historical facial skin images and current facial skin images, a facial skin condition is identified by the facial skin analysis module 258, and correlated with known facial skin conditions stored in memory 252. The facial skin analysis module may identify treatment options for the facial skin condition and deliver feedback to the occupant through a speaker 222, the user interface 208, as an SMS message to a cell phone, by an email, or the like.

At step 590, a determination is made as to whether the sensors detect another occupant. If further occupants are detected, then the occupant number is incremented. If no further occupants are detected, the facial skin conditions of each occupant are stored in memory and also transmitted to the onboard communication module for further analysis of the causes and treatments by the facial skin analysis application 365. The communication between a vehicle 140 and the facial skin analysis application 165 is made over communication channels $105_a$ ($105_{1a}$, $105_{2a}$, etc.) A data packet containing the facial skin images and facial skin conditions as identified by the vehicle facial analysis system are also be transmitted to the data lake 160 as shown by the dotted arrows representing communication channels $105_b$ in FIG. 1.

Figure 6:
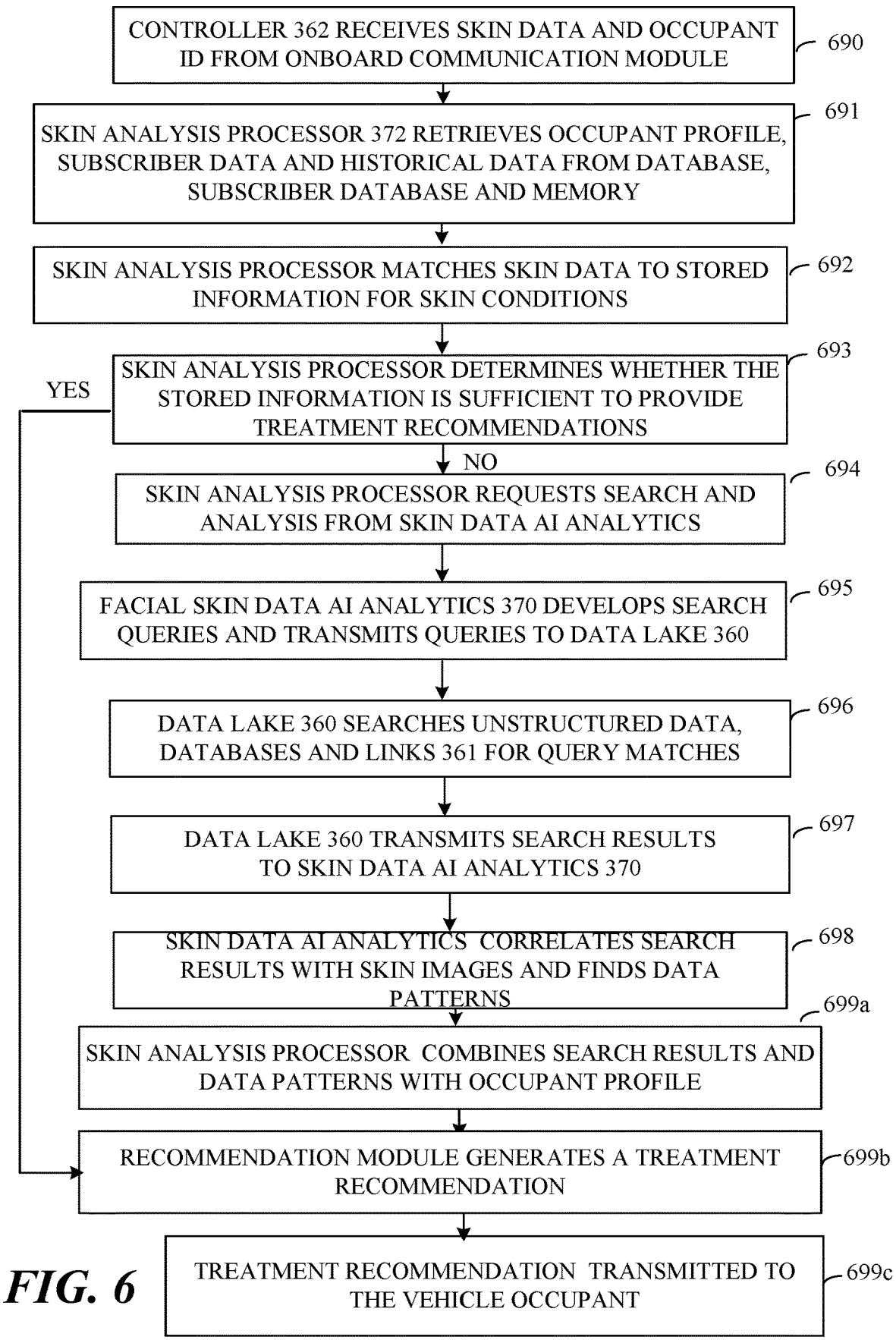
FIG. 6 is an exemplary flowchart of the process by which the facial skin condition data is further analyzed by the facial skin analysis application, according to certain embodiments.

FIG. 6 is a flowchart detailing the process by which the facial skin condition data from vehicle 140 is further analyzed by the facial skin analysis application 165 at the data center 130.

At step 690, the controller 362 receives facial skin images, preliminary facial skin condition and occupant identification from onboard communication module 210. At step 691, the facial skin analysis processor 372 retrieves the occupant profile, subscriber data and historical data from database, subscriber database and memory respectively. At step 692, the facial skin analysis processor matches the facial skin condition to stored causes of the facial skin condition, if any. At step 693, the facial skin analysis processor determines whether the stored information is sufficient to provide recommendations. If YES, the process moves to step 699c in which treatment recommendations are made. If NO, the process moves to step 694, where the facial skin analysis processor recommends searching for more information by the skin data AI analytics module(s) 370. At step 695, the skin data analytics program 170 develops search queries and transmits the queries to the data lake 360. At step 696, the data lake 360 searches databases and links 361 for query matches. At step 697, the data lake 360 transmits search results to skin data analytics 170. At step 698, skin data analytics 170 correlates search results with the skin images to determine patterns of facial skin conditions and treatments, products or other skin information. At step 699a, the skin analysis processor combines the determined facial skin conditions and treatments, products or other skin information with the vehicle occupant profile. At step 699b, the recommendation module 374 generates a treatment recommendation. At step 699c, the treatment recommendation is sent to controller 362 for transmission to the seat occupant.

Treatment recommendations may include a report of the facial skin conditions, causes for the facial skin conditions, treatments of the facial skin conditions and recommendations to skin care professionals or products for treating the facial skin conditions.

The first embodiment is illustrated with respect to FIG. 1 through FIG. 6. The first embodiment describes a method for improving facial skin conditions using interior vehicle cameras 232 (FIG. 2A, 2B), comprising imaging the facial skin of at least one vehicle seat occupant by at least one vehicle camera each time the vehicle occupant occupies a seat in the vehicle, storing (in memory 252, FIG. 2A), storing the images of the facial skin with timestamps of the images, comparing each current image with at least one stored image having an earlier timestamp, detecting changes between the current image and the at least one stored image having an earlier timestamp, accessing, from a vehicle memory 252, facial skin data which includes facial skin conditions based on at least one of age, gender, ethnic origins and medical diseases affecting the facial skin, matching the changes to at least one facial skin condition (from memory 252, FIG. 2A, and/or by using skin analysis application 365 (FIG. 1, 3A), accessing treatment options for the facial skin condition, accessing facial skincare product information for the facial skin condition, determining a facial skin treatment recommendation (by skin analysis module 258, FIG. 2A or by facial skin analysis application 365, FIG. 3A) based on the at least one facial skin condition, the treatment options and facial skincare product information (from memory 252, FIG. 2A, and/or from data lake 360 connections to skin and medical databases, FIG. 3B), and notifying the vehicle seat occupant of the facial skin changes, the facial skin condition and the facial skin treatment recommendation (through user interface 208 or by direct communication with a seat occupant's smart device by controller 362).

The method includes comparing each current image with at least one stored image having an earlier timestamp in a range selected from at least one of: greater than two weeks and less than five years before the current image, greater than one month and less than three months before the current image and greater than six months and less than one year before the current image. Alternatively the method includes comparing each current image with each stored image having an earlier timestamp until one of a change is detected and all stored images have been compared to the current image.

The method includes accessing further facial skin data by transmitting the facial skin images and the changes by an onboard communications module 210 of the vehicle to a facial skin analysis application 365, additionally transmitting the facial skin images to a data lake 360, requesting, by the facial skin analysis application, a search of the data lake for facial skin information related to the facial skin images and the changes, receiving the request by a facial skin data artificial intelligence (AI) analytics module 370, querying, by the facial skin data AI analytics module, the data lake for information relating to the facial skin images and the changes, treatment options and skincare products, searching, within the data lake, unstructured data and structured databases for matches to the query, retrieving, by the facial skin data AI analytics module, the matches to the query, analyzing, by the facial skin data AI analytics module, the matches to determine a skin condition, treatment options for the skin condition and facial skincare product information related to the skin condition, receiving, by the facial skin analysis application, the skin condition, treatment options for the skin condition and facial skincare product information, accessing a profile of a vehicle seat occupant (from vehicle memory 252 or from database 364 or subscriber data 367), correlating the profile with the treatment options and facial skincare product information to generate the facial skin treatment recommendation, transmitting, by the facial skin analysis application, the facial skin treatment recommendation to the onboard communications module 210 of the vehicle, receiving the facial skin treatment recommendation by the onboard communications module, and updating the memory of the vehicle.

In another alternative, the method includes accessing facial skin data from a memory 252 of a control system (see CPU 250, FIG. 2A) of the vehicle.

Alternatively, the method includes registering (462, FIG. 4), through a smart device of the vehicle seat occupant, with a facial skin analysis application 365, receiving, by the facial skin analytics application, the facial skin images and the changes from an onboard communication module 210 of the vehicle 140, also transmitting the facial skin images to a data lake, requesting, by the facial skin analysis application 365, a search related to the facial skin images and changes, receiving, by a facial skin data artificial intelligence (AI) analytics program, the request, querying, by the facial skin data AI analytics module, the data lake 360 for information relating to the facial skin images and the changes, treatment options and skincare products, searching, within the data lake, unstructured data and structured databases (361A-361i) for matches to the query, retrieving, by the facial skin data AI analytics module, the matches to the query, analyzing, by the facial skin data AI analytics module, the matches to the query to determine a skin condition, treatment options for the skin condition and facial skincare product information related to the skin condition, receiving, by the facial skin analysis application, the skin condition, treatment options for the skin condition and facial skincare product information, accessing a profile of a vehicle seat occupant, correlating the profile with the treatment options and facial skincare product information to generate the facial skin treatment recommendation (374, FIG. 3A), and transmitting the recommendation to the smart device of the registered vehicle seat occupant.

Registering with the facial skin analysis application by a smart device of a vehicle seat occupant further comprises creating public and private pair keys (462, FIG. 4) with a smart device of the vehicle seat occupant, transmitting the public key to the facial skin analysis application, creating a user profile 464 including age, weight, gender, ethnic origins, previous skin and medical diseases of the vehicle seat occupant, and providing a list 466 of preferred medical practitioners, dermatologists, cosmetologists and skin care professionals, and retail outlets 467.

The facial skin treatment recommendation further comprises at least one of recommending a dermatologist based on a home location or a current location of the vehicle occupant, recommending a cosmetologist based on a home location or a current location of the vehicle occupant, recommending a medical professional based on a home location or a current location of the vehicle occupant, recommending facial skin care products, recommending brands of concealing make-up, recommending stress relief therapy, and recommending a facial skin care regime.

The second embodiment is illustrated with respect to FIG. 1 through FIG. 6. The second embodiment describes a system for improving facial skin conditions using interior vehicle cameras, comprising a plurality of vehicles ($140_1$-$140_n$, FIG. 1), each vehicle including a plurality of cameras ($232_1$-$232_n$, FIG. 2B), each camera having a field of view focused at the face of a vehicle seat occupant, each camera configured to record facial skin images of the seat occupant. The system further includes a plurality of sensors (202, 204, 206, FIG. 2A) for sensing the presence of a seat occupant, a CPU 250 operatively connected with: the plurality of cameras and the plurality of sensors, a memory 252 including a database previously stored facial skin images of each seat occupant, a user profile, known facial skin conditions based on at least one of age, gender, ethnic origins and medical diseases affecting the facial skin, an image processor 256 configured to receive and timestamp the current facial skin images and store the current facial skin images and timestamps in the memory 252, an identity module 254 configured to match the current facial skin images of each seat occupant to the previously stored facial skin images to identify the seat occupant, an image comparison module 257 configured to compare the current facial skin images of each identified vehicle seat occupant with the previously stored facial skin images of the identified vehicle seat occupant and detect changes in facial skin features of the identified vehicle seat occupant, a skin analysis module 258 configured to determine a facial skin condition of the identified vehicle seat occupant based on the changes in the features, a user interface 208 configured to communicate with the identified vehicle seat occupant, an onboard communications module 210 configured to transmit a data packet including the facial skin condition, current facial skin images and previously stored facial skin images of each identified seat occupant and to receive treatment recommendations.

The system further includes a facial skin analysis application 365 (FIG. 3A) configured to receive the data packet and request a search of a data lake for information related to the facial skin condition, current facial skin images and previously stored facial skin images, a skin data artificial intelligence (AI) analytics module 370 (FIG. 3A, 3B) configured to receive the request and form search queries, a data lake 360 configured to receive the search queries, search for facial skin information from a plurality of sources (unstructured data stored in the data lake and structured data obtained from databases $361_A$-$361_F$, FIG. 3B) based on the search queries and transmit the matches to the facial skin data AI analytics module 370. The facial skin data AI analytics module is further configured to analyze the matches and determine a skin condition, treatment options for the skin condition and facial skincare product information related to the skin condition. The facial skin analysis application is further configured to receive the skin condition, treatment options for the skin condition and facial skincare product information related to the skin condition, access a user profile of the identified seat occupant, and correlate the skin condition, treatment options for the skin condition and facial skincare product information related to the skin condition with the user profile, a treatment recommendation module is configured to generate a facial skin treatment recommendation (see recommendation module 374, FIG. 3A) for each identified seat occupant. The facial skin analysis application 365 is further configured to transmit the facial skin treatment recommendation of each identified vehicle seat occupant to the respective onboard communications module 210. The onboard communications module provides the facial skin recommendation to each identified vehicle seat occupant of each vehicle and updates the vehicle memory.

The facial skin treatment recommendation module is further configured to recommend at least one of a dermatologist based on a home location or a current location of the vehicle seat occupant, a cosmetologist based on a home location or a current location of the vehicle seat occupant, a medical professional based on a home location or a current location of the vehicle seat occupant, facial skin care products and purchasing information for the facial skin care products, brands of concealing make-up and purchasing information for the concealing make-up, stress relief therapy, and a skin care regime.

The facial skin analysis application further comprises a registration module 363 configured to register each of the plurality of vehicles with the facial skin analysis application, a database 367 of subscriber information, the subscriber information including the user profile of each vehicle seat occupant of each of the plurality of vehicles, wherein the facial skin analysis application further correlates the subscriber information with the facial skin conditions of each identified vehicle seat occupant in determining the facial skin recommendation of the identified vehicle seat occupant.

The data lake stores the facial skin conditions and facial skin recommendations of each of the identified vehicle seat occupants of each of the plurality of vehicles.

The registration module is further configured to register a vehicle occupant travelling in any of the plurality of vehicles ($140_1$-$140_n$, FIG. 1), with the facial skin analysis application 365, through a smart device of the vehicle occupant and retrieve a user profile from the smart device, wherein the facial skin analysis application is further configured to receive and store current timestamped facial skin images of the registered vehicle occupant in a facial skin analysis application memory when the registered vehicle occupant travels in any of the plurality of vehicles; detect feature changes between the current timestamped facial skin images and previously stored facial skin images of the registered vehicle occupant, request a search by the skin data AI analytics module 370 for information related to the feature changes, wherein the facial skin data AI analytics module is further configured to form search queries based on the feature changes and transmit the search queries to the data lake 360, wherein the data lake is configured to receive the search queries, search for facial skin information from a plurality of sources for matches to the search queries and transmit the matches to the facial skin data AI analytics module, wherein the facial skin data AI analytics module is further configured to analyze the matches and determine a skin condition, treatment options for the skin condition and facial skincare product information related to the skin condition, wherein the facial skin analysis application is further configured to receive the skin condition, treatment options for the skin condition and facial skincare product information related to the skin condition and correlate the skin condition, treatment options for the skin condition and facial skincare product information related to the skin condition with the user profile, wherein the treatment recommendation module is configured to generate a facial skin treatment recommendation, wherein the facial skin analysis application is further configured to transmit the facial skin treatment recommendation of the registered vehicle occupant to the smart device of the registered vehicle occupant.

The registration module 363 is further configured to register the vehicle occupant by receiving a public key (step 462, FIG. 4) from the smart device, request personal information (create user profile, 464) from the vehicle occupant including age, weight, gender, ethnic origins, previous skin and medical diseases of the vehicle seat occupant, request lists of preferred medical practitioners, dermatologists, cosmetologists and skin care professionals (step 466), and retail outlets (step 467), and store the public key, personal information and lists in a subscriber database 367 (FIG. 3A).

The previously timestamped skin facial images are from a time period preferably in the range of one hour to five years, more preferably in the range of one hour to one year, most preferably in the range of one hour to two months.

The plurality of sensors include at least one of weight sensors 202 located in each seat, fingerprint sensors 204 on the steering wheel, a fingerprint reader on the user interface 208, a breathalyzer, audio sensors and heart rate sensors (other sensors, 206, FIG. 2A), wherein the identity module 254 is further configured to match information from the at least one sensor with previously stored sensor profiles of vehicle seat occupants to identify a current vehicle seat occupant and retrieve the user profile of the current vehicle seat occupant, the user profile including the age, weight and height of the current vehicle seat occupant and wherein the CPU 250 adjusts the field of view of the camera 232 of the current vehicle seat occupant based on the height.

The third embodiment is illustrated with respect to FIG. 1 through FIG. 10. The third embodiment describes a non-transitory computer readable medium having instructions stored therein that, when executed by one or more processor, cause the one or more processors to perform a method for improving facial skin conditions using vehicle cameras, comprising imaging the facial skin of at least one vehicle seat occupant by at least one vehicle camera 140 each time the vehicle occupant occupies a seat in the vehicle, storing the images of the facial skin with timestamps of the images, comparing each current image with at least one stored image of the vehicle seat occupant having an earlier timestamp, detecting changes between the current image and the at least one stored image having an earlier timestamp, determining a facial skin condition based on the changes, accessing facial skin data which includes facial skin conditions based on at least one of age, gender, ethnic origins and medical diseases affecting the facial skin, matching the changes to at least one facial skin condition, accessing treatment options for the facial skin condition, accessing facial skincare product information for the facial skin condition, determining a facial skin treatment recommendation based on the at least one facial skin condition, the treatment options and facial skincare product information, and notifying the vehicle seat occupant of the facial skin changes, the facial skin condition and the facial skin treatment recommendation.

The non-transitory computer readable medium method further comprises transmitting the facial skin images and the changes by an onboard communications module 210 of the vehicle to a facial skin analysis application 365, transmitting the facial skin images to a data lake 360, requesting, by the facial skin analysis application, a search of the data lake for facial skin information related to the facial skin images and the facial skin changes, receiving the request by a facial skin data artificial intelligence (AI) analytics module 370, querying, by the facial skin data AI analytics module, the data lake for information relating to the facial skin images and the facial skin changes, treatment options and skincare products, searching, within the data lake, unstructured data and structured databases for matches to the query, retrieving, by the facial skin data AI analytics module, the matches to the query, analyzing, by the facial skin data AI analytics module, the matches to determine a skin condition, treatment options for the skin condition and facial skincare product information related to the skin condition, receiving, by the facial skin analysis application, the skin condition, treatment options for the skin condition and facial skincare product information, accessing a user profile of a vehicle seat occupant, correlating the user profile with the treatment options and facial skincare product information to generate the facial skin treatment recommendation, transmitting, by the facial skin analysis application, the facial skin treatment recommendation to the onboard communications module of the vehicle, receiving the facial skin treatment recommendation by the onboard communications module, and updating the memory of the vehicle.

The non-transitory computer readable medium method further comprises registering, through a smart device of the vehicle seat occupant, with the facial skin analysis application; creating a user profile including age, weight, gender, ethnic origins, previous skin and medical diseases of the vehicle seat occupant, receiving, by the facial skin analytics application, the facial skin images and the changes from an onboard communication module of the vehicle, transmitting the facial skin images to the data lake, requesting, by the facial skin analysis application, a search related to the facial skin images and changes, receiving, by the facial skin data artificial intelligence (AI) analytics program, the request, querying, by the facial skin data AI analytics module, the data lake for information related to the facial skin images and the changes, treatment options and skincare products, searching, within the data lake, unstructured data and structured databases for matches to the query, retrieving, by the facial skin data AI analytics module, the matches to the query, analyzing, by the facial skin data AI analytics module, the matches to the query to determine a skin condition, treatment options for the skin condition and facial skincare product information related to the skin condition, receiving, by the facial skin analysis application, the skin condition, treatment options for the skin condition and facial skincare product information, accessing the user profile of the vehicle seat occupant, correlating the user profile with the treatment options and facial skincare product information to generate the facial skin treatment recommendation, and transmitting the recommendation to the smart device of the registered vehicle seat occupant.

Registering with the facial skin analysis application by a vehicle seat occupant further comprises creating public and private pair keys with a smart device of the vehicle seat occupant, transmitting the public key to the facial skin analysis application, and providing a list of preferred medical practitioners, dermatologists, cosmetologists and skin care professionals, and retail outlets.

Figure 7:
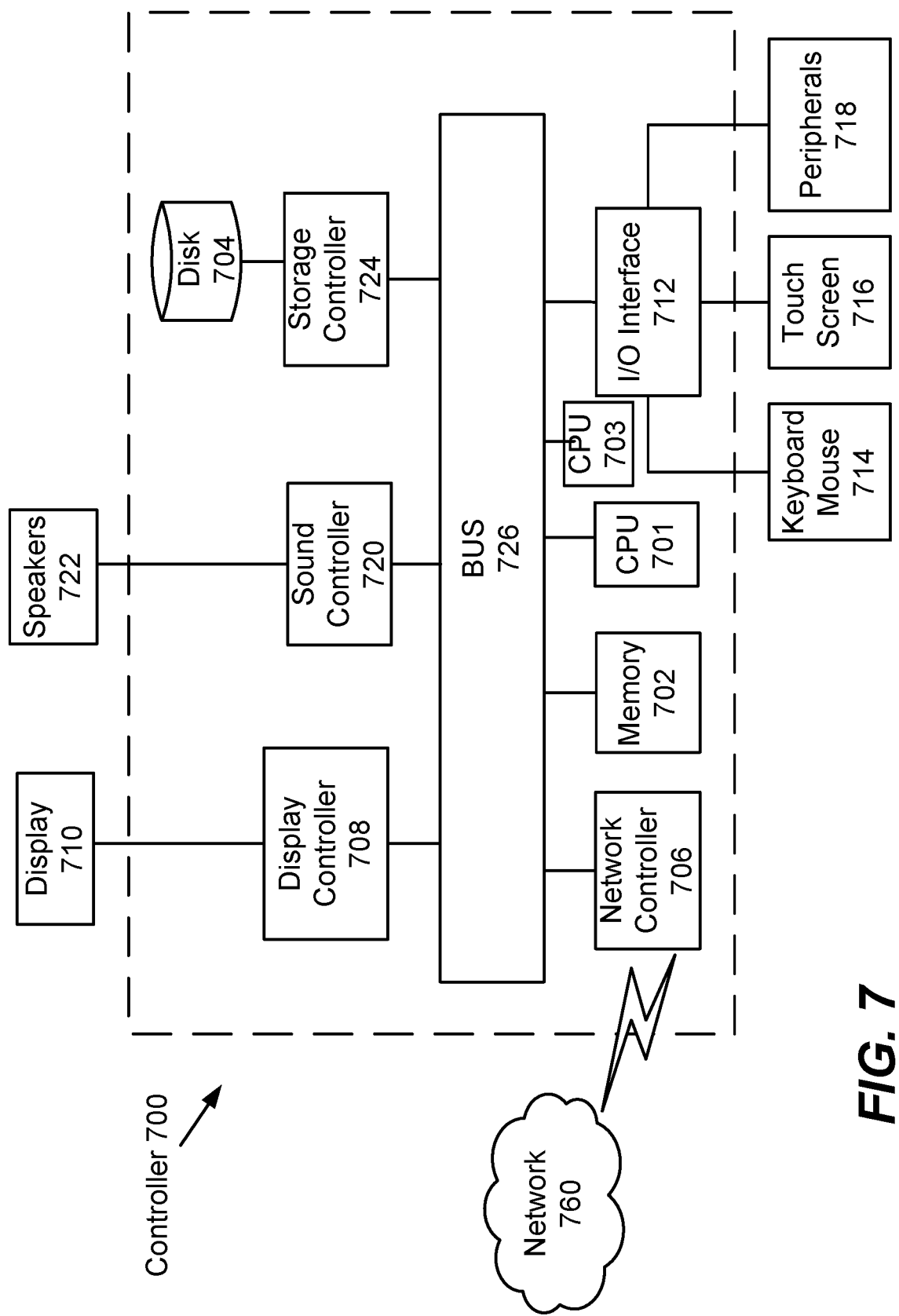
FIG. 7 is an illustration of a non-limiting example of details of computing hardware used in the computing systems, according to certain embodiments.

Next, further details of the hardware description of the computing environments of FIG. 2A and FIG. 3A according to exemplary embodiments are described with reference to FIG. 7. In FIG. 7, a controller 700 is described which is representative of the controller 250 of FIG. 1 or the controller 362 of FIG. 3A in which the controller 700 is a computing device which includes a CPU 701 which performs the processes described above/below. The process data and instructions may be stored in memory 702. These processes and instructions may also be stored on a storage medium disk 704 such as a hard drive (HDD) or portable storage medium or may be stored remotely.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claims may be provided as a utility application, background daemon, or component of an operating system, or combination thereof, executing in conjunction with CPU 701, 703 and an operating system such as Microsoft Windows 7, UNIX, Solaris, LINUX, Apple MAC-OS and other systems known to those skilled in the art.

The hardware elements in order to achieve the computing device may be realized by various circuitry elements, known to those skilled in the art. For example, CPU 701 or CPU 703 may be a Xenon or Core processor from Intel of America or an Opteron processor from AMD of America, or may be other processor types that would be recognized by one of ordinary skill in the art. Alternatively, the CPU 701, 703 may be implemented on an FPGA, ASIC, PLD or using discrete logic circuits, as one of ordinary skill in the art would recognize. Further, CPU 701, 703 may be implemented as multiple processors cooperatively working in parallel to perform the instructions of the inventive processes described above.

The computing device in FIG. 7 also includes a network controller 706, such as an Intel Ethernet PRO network interface card from Intel Corporation of America, for interfacing with network 760. As can be appreciated, the network 760 can be a public network, such as the Internet, or a private network such as an LAN or WAN network, or any combination thereof and can also include PSTN or ISDN sub-networks. The network 760 can also be wired, such as an Ethernet network, or can be wireless such as a cellular network including EDGE, 3G, 4G and 5G wireless cellular systems. The wireless network can also be Wi-Fi, Bluetooth, or any other wireless form of communication that is known.

The computing device further includes a display controller 708, such as a NVIDIA GeForce GTX or Quadro graphics adaptor from NVIDIA Corporation of America for interfacing with display 710, such as a Hewlett Packard HPL2445w LCD monitor or any type of computer monitor. A general purpose I/O interface 712 interfaces with a keyboard and/or mouse 714 as well as a touch screen panel 716 on or separate from display 710. General purpose I/O interface also connects to a variety of peripherals 718 including printers and scanners, such as an Officejet or DeskJet from Hewlett Packard.

A sound controller 720 is also provided in the computing device such as Sound Blaster X-Fi Titanium from Creative, to interface with speakers/microphone 722 thereby providing sounds and/or music.

The general purpose storage controller 724 connects the storage medium disk 704 with communication bus 726, which may be an ISA, EISA, VESA, PCI, or similar, for interconnecting all of the components of the computing device. A description of the general features and functionality of the display 710, keyboard and/or mouse 714, as well as the display controller 708, storage controller 724, network controller 706, sound controller 720, and general purpose I/O interface 712 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 8.

Figure 8:
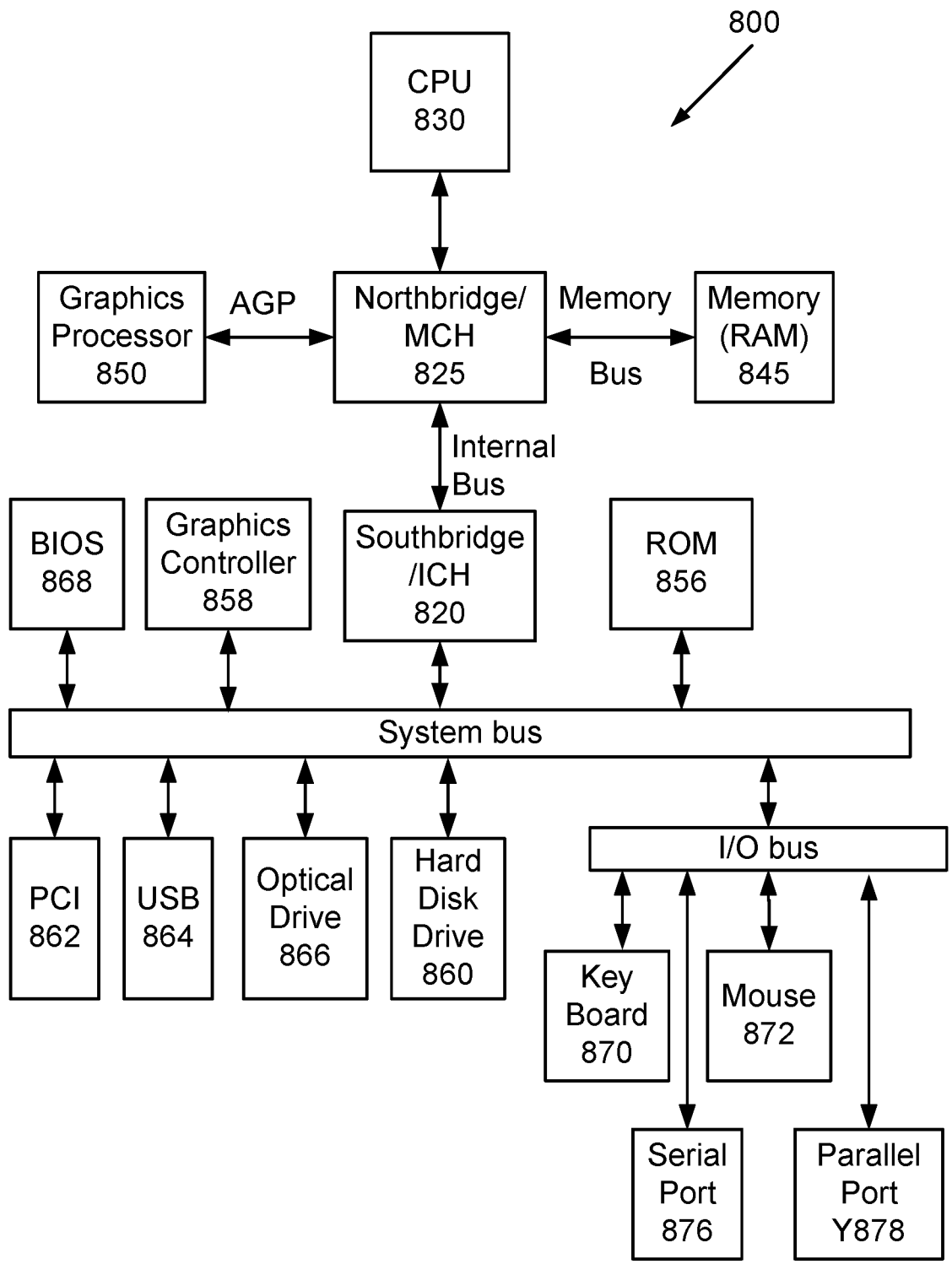
FIG. 8 is an exemplary schematic diagram of a data processing system used within the computing system, according to certain embodiments.

FIG. 8 shows a schematic diagram of a data processing system, according to certain embodiments, for performing the functions of the exemplary embodiments. The data processing system is an example of a computer in which code or instructions implementing the processes of the illustrative embodiments may be located.

In FIG. 8, data processing system 800 employs a hub architecture including a north bridge and memory controller hub (NB/MCH) 825 and a south bridge and input/output (I/O) controller hub (SB/ICH) 820. The central processing unit (CPU) 830 is connected to NB/MCH 825. The NB/MCH 825 also connects to the memory 845 via a memory bus, and connects to the graphics processor 850 via an accelerated graphics port (AGP). The NB/MCH 825 also connects to the SB/ICH 820 via an internal bus (e.g., a unified media interface or a direct media interface). The CPU Processing unit 830 may contain one or more processors and even may be implemented using one or more heterogeneous processor systems.

Figure 9:
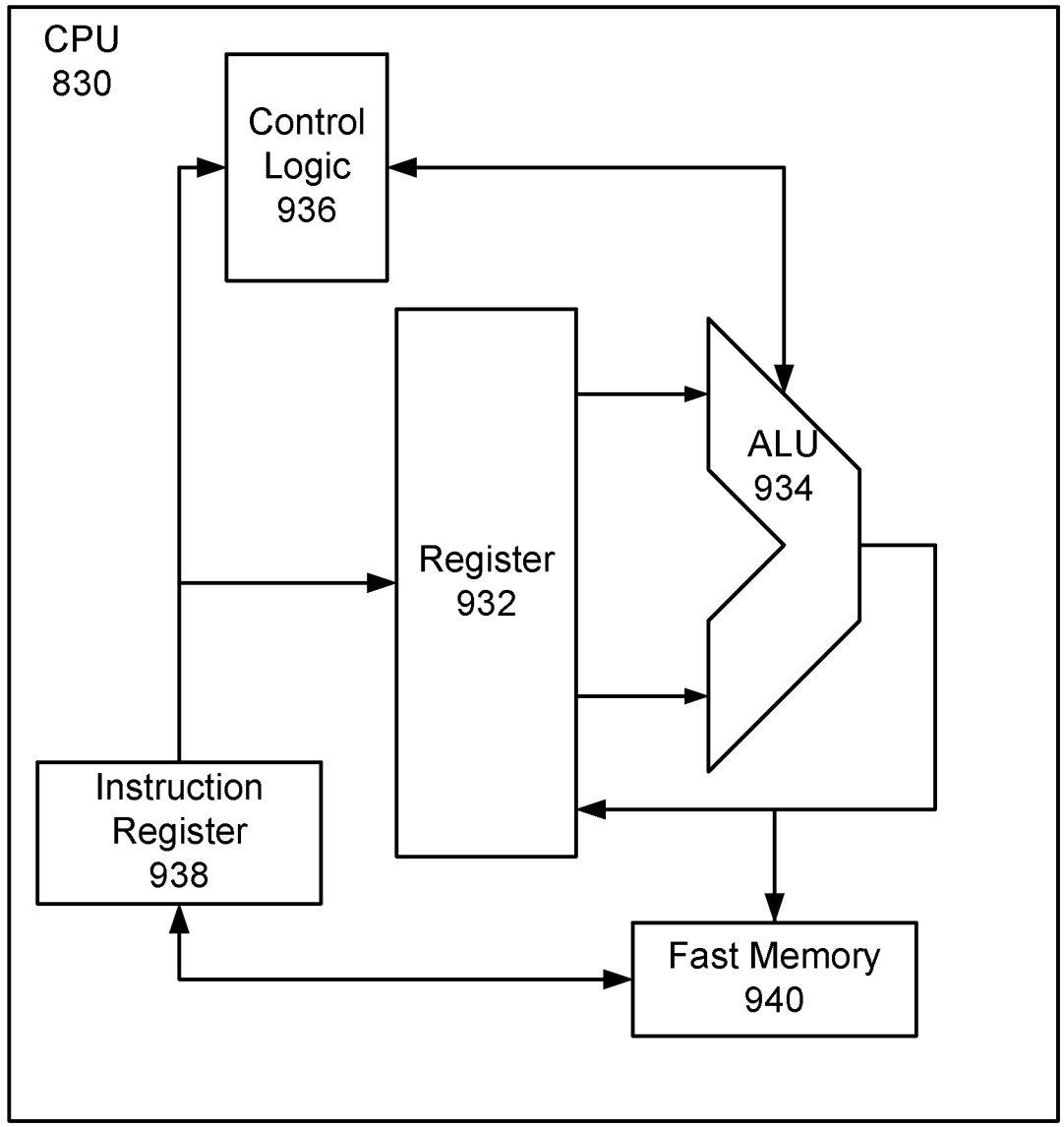
FIG. 9 is an exemplary schematic diagram of a processor used with the computing system, according to certain embodiments.

For example, FIG. 9 shows one implementation of CPU 830. In one implementation, the instruction register 938 retrieves instructions from the fast memory 940. At least part of these instructions are fetched from the instruction register 938 by the control logic 936 and interpreted according to the instruction set architecture of the CPU 830. Part of the instructions can also be directed to the register 932. In one implementation the instructions are decoded according to a hardwired method, and in another implementation the instructions are decoded according a microprogram that translates instructions into sets of CPU configuration signals that are applied sequentially over multiple clock pulses. After fetching and decoding the instructions, the instructions are executed using the arithmetic logic unit (ALU) 934 that loads values from the register 932 and performs logical and mathematical operations on the loaded values according to the instructions. The results from these operations can be feedback into the register and/or stored in the fast memory 940. According to certain implementations, the instruction set architecture of the CPU 830 can use a reduced instruction set architecture, a complex instruction set architecture, a vector processor architecture, a very large instruction word architecture. Furthermore, the CPU 830 can be based on the Von Neuman model or the Harvard model. The CPU 830 can be a digital signal processor, an FPGA, an ASIC, a PLA, a PLD, or a CPLD. Further, the CPU 830 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 8, the data processing system 800 can include that the SB/ICH 820 is coupled through a system bus to an I/O Bus, a read only memory (ROM) 856, universal serial bus (USB) port 864, a flash binary input/output system (BIOS) 868, and a graphics controller 858. PCI/PCIe devices can also be coupled to SB/ICH 888 through a PCI bus 862.

The PCI devices may include, for example, Ethernet adapters, add-in cards, and PC cards for notebook computers. The Hard disk drive 860 and CD-ROM 866 can use, for example, an integrated drive electronics (IDE) or serial advanced technology attachment (SATA) interface. In one implementation the I/O bus can include a super I/O (SIO) device.

Further, the hard disk drive (HDD) 860 and optical drive 866 can also be coupled to the SB/ICH 820 through a system bus. In one implementation, a keyboard 870, a mouse 872, a parallel port 878, and a serial port 876 can be connected to the system bus through the I/O bus. Other peripherals and devices that can be connected to the SB/ICH 820 using a mass storage controller such as SATA or PATA, an Ethernet port, an ISA bus, a LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry, or based on the requirements of the intended back-up load to be powered.

Figure 10:
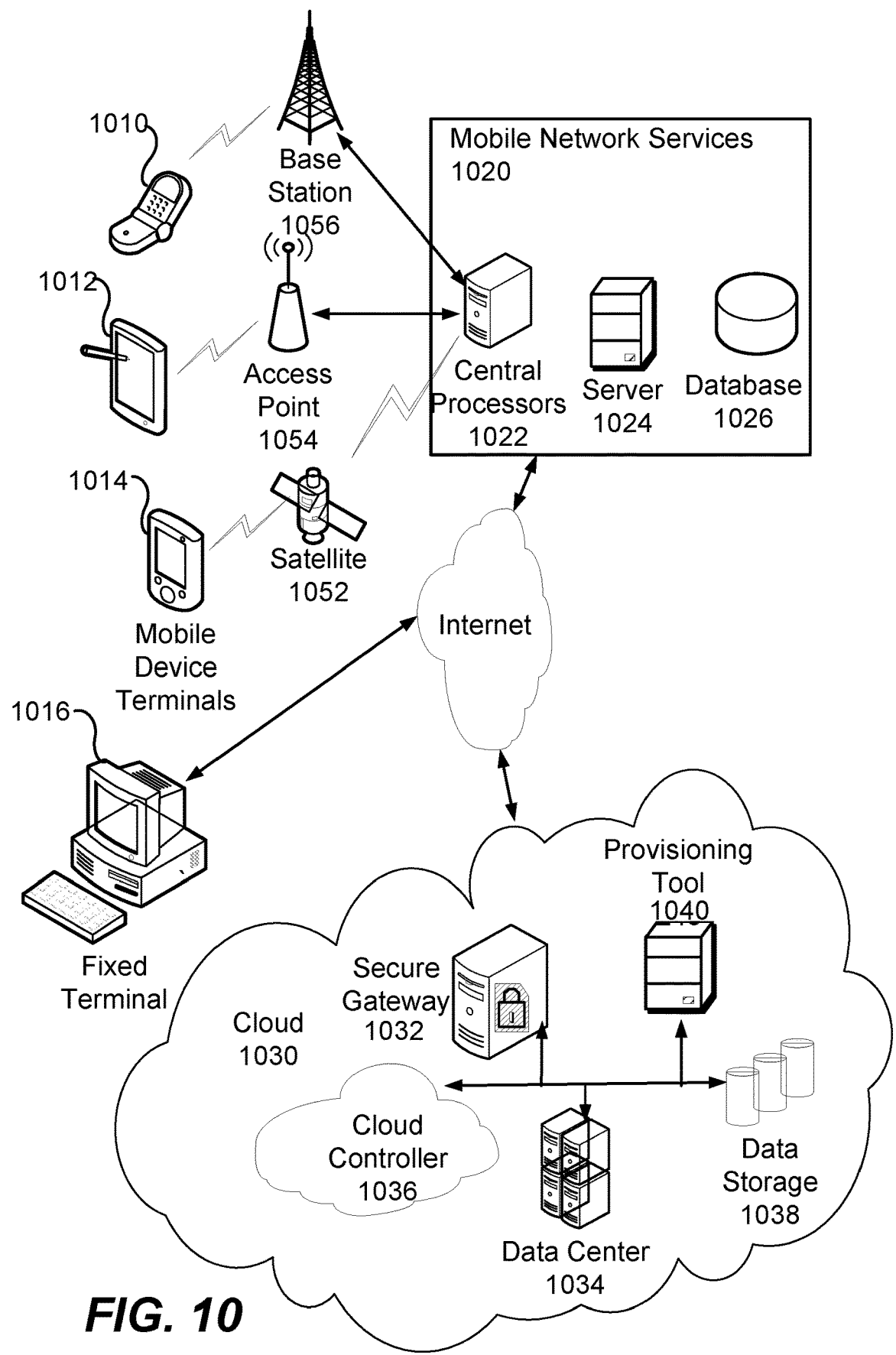
FIG. 10 is an illustration of a non-limiting example of distributed components which may share processing with the controller, according to certain embodiments.

The functions and features described herein may also be executed by various distributed components of a system. For example, one or more processors may execute these system functions, wherein the processors are distributed across multiple components communicating in a network. The distributed components may include one or more client and server machines, which may share processing, as shown by FIG. 10, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

The above-described hardware description is a non-limiting example of corresponding structure for performing the functionality described herein.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A method for improving facial skin conditions using vehicle cameras, comprising:
   imaging a facial skin of at least one vehicle seat occupant by at least one vehicle camera each time the vehicle occupant occupies a seat in the vehicle;
   storing images of the facial skin with timestamps of the images;
   comparing each current image with at least one stored image having an earlier timestamp;
   detecting changes between the current image and the at least one stored image having the earlier timestamp;
   accessing, from a vehicle memory, facial skin data which includes facial skin conditions based on at least one of age, gender, ethnic origins and medical diseases affecting the facial skin;
   matching the changes to at least one facial skin condition;
   accessing treatment options for the at least one facial skin condition;
   accessing facial skincare product information for the at least one facial skin condition;
   determining a facial skin treatment recommendation based on the at least one facial skin condition, the treatment options and the facial skincare product information; and
   notifying the vehicle seat occupant of the facial skin changes, the at least one facial skin condition and the facial skin treatment recommendation.

2. The method of claim 1, further comprising:
   comparing each current image with at least one stored image having an earlier timestamp in a range selected from at least one of:
   greater than two weeks and less than five years before the current image;
   greater than one month and less than three months before the current image; and
   greater than six months and less than one year before the current image.

3. The method of claim 1, further comprising:
   comparing each current image with each stored image having an earlier timestamp until one of a change is detected and all stored images have been compared to the current image.

4. The method of claim 1, further comprising:
   transmitting the facial skin images and the changes by an onboard communications circuitry of the vehicle to a facial skin analysis application;
   transmitting the facial skin images to a data lake;
   requesting, by the facial skin analysis application, a search of the data lake for facial skin information related to the facial skin images and the changes;
   receiving the request by a facial skin data artificial intelligence (AI) analytics circuitry;
   querying, by the facial skin data AI analytics circuitry, the data lake for information relating to the facial skin images and the changes, treatment options and skincare products;
   searching, within the data lake, unstructured data and structured databases for matches to the query;
   retrieving, by the facial skin data AI analytics circuitry, the matches to the query;
   analyzing, by the facial skin data AI analytics circuitry, the matches to determine a skin condition, treatment options for the skin condition and facial skincare product information related to the skin condition;
   receiving, by the facial skin analysis application, the skin condition, treatment options for the skin condition and facial skincare product information;
   accessing a profile of a vehicle seat occupant;
   correlating the profile with the treatment options and facial skincare product information to generate the facial skin treatment recommendation;
   transmitting, by the facial skin analysis application, the facial skin treatment recommendation to the onboard communications circuitry of the vehicle;
   receiving the facial skin treatment recommendation by the onboard communications circuitry; and
   updating the memory of the vehicle.

5. The method of claim 1, further comprising:
   accessing facial skin data from a memory of a control system of the vehicle.

6. The method of claim 1, further comprising:
   registering, through a smart device of the vehicle seat occupant, with a facial skin analysis application;
   receiving, by the facial skin analytics application, the facial skin images and the changes from an onboard communication circuitry of the vehicle;
   transmitting the facial skin images to a data lake;
   requesting, by the facial skin analysis application, a search related to the facial skin images and changes;
   receiving, by a facial skin data artificial intelligence (AI) analytics program, the request;
   querying, by the facial skin data AI analytics circuitry, the data lake for information relating to the facial skin images and the changes, treatment options and skincare products;

searching, within the data lake, unstructured data and structured databases for matches to the query;

retrieving, by the facial skin data AI analytics circuitry, the matches to the query;

analyzing, by the facial skin data AI analytics circuitry, the matches to the query to determine a skin condition, treatment options for the skin condition and facial skincare product information related to the skin condition;

receiving, by the facial skin analysis application, the skin condition, treatment options for the skin condition and facial skincare product information;

accessing a profile of a vehicle seat occupant;

correlating the profile with the treatment options and facial skincare product information to generate the facial skin treatment recommendation; and transmitting the recommendation to the smart device of the registered vehicle seat occupant.

7. The method of claim 6, wherein registering with the facial skin analysis application by a vehicle seat occupant further comprises:

creating public and private pair keys with a smart device of the vehicle seat occupant;

transmitting the public key to the facial skin analysis application;

creating a user profile including age, weight, gender, ethnic origins, previous skin and medical diseases of the vehicle seat occupant; and providing a list of preferred medical practitioners, dermatologists, cosmetologists and skin care professionals, and retail outlets.

8. The method of claim 1, wherein the facial skin treatment recommendation further comprises at least one of:

recommending a dermatologist based on a home location or a current location of the vehicle occupant;

recommending a cosmetologist based on a home location or a current location of the vehicle occupant;

recommending a medical professional based on a home location or a current location of the vehicle occupant;

recommending facial skin care products;

recommending brands of concealing make-up;

recommending stress relief therapy; and recommending a facial skin care regime.

9. A system for improving facial skin conditions using vehicle cameras, comprising a plurality of vehicles, each vehicle including:

a plurality of cameras, each camera having a field of view focused at a face of a vehicle seat occupant, each camera configured to record current facial skin images of the vehicle seat occupant;

a plurality of sensors for sensing the presence of a vehicle seat occupant;

a CPU operatively connected with the plurality of cameras and the plurality of sensors;

a memory including a database of previously stored facial skin images of each vehicle seat occupant, a user profile, known facial skin conditions based on at least one of age, gender, ethnic origins and medical diseases affecting the facial skin;

an image processor configured to receive and timestamp the current facial skin images and store the current facial skin images and timestamps in the memory;

an identity circuitry configured to match the current facial skin images of each vehicle seat occupant to the previously stored facial skin images to identify the vehicle seat occupant;

an image comparison circuitry configured to compare the current facial skin images of each identified vehicle seat occupant with the previously stored facial skin images of the identified vehicle seat occupant and detect changes in facial skin features of the identified vehicle seat occupant;

a skin analysis circuitry configured to determine a facial skin condition of the identified vehicle seat occupant based on the changes in the facial skin features;

a user interface configured to communicate with the identified vehicle seat occupant;

an onboard communications circuitry configured to transmit a data packet including the facial skin condition, current facial skin images and previously stored facial skin images of each identified seat occupant and to receive treatment recommendations;

a facial skin analysis application configured to receive the data packet and request a search of a data lake for information related to the facial skin condition, current facial skin images and previously stored facial skin images;

a skin data artificial intelligence (AI) analytics circuitry configured to receive the request and form search queries;

a data lake configured to receive the search queries, search for facial skin information from a plurality of sources for matches to the search queries and transmit the matches to the facial skin data AI analytics circuitry;

wherein the facial skin data AI analytics circuitry is further configured to analyze the matches and determine a skin condition, treatment options for the skin condition and facial skincare product information related to the skin condition;

wherein the facial skin analysis application is further configured to receive the skin condition, treatment options for the skin condition and facial skincare product information related to the skin condition, access a user profile of the identified vehicle seat occupant, and correlate the skin condition, treatment options for the skin condition and facial skincare product information related to the skin condition with the user profile;

a treatment recommendation circuitry configured to generate a facial skin treatment recommendation;

wherein the facial skin analysis application is further configured to transmit the facial skin treatment recommendation of each identified vehicle seat occupant to the respective onboard communications circuitry; and wherein the onboard communications circuitry provides the facial skin recommendation to the identified vehicle seat occupant and updates the vehicle memory.

10. The system of claim 9, wherein the facial skin treatment recommendation circuitry is further configured to recommend at least one of a dermatologist based on a home location or a current location of the identified vehicle occupant;

a cosmetologist based on a home location or a current location of the identified vehicle;

a medical professional based on a home location or a current location of the identified vehicle;

facial skin care products and purchasing information for the facial skin care products;

brands of concealing make-up and purchasing information for the concealing make-up;

stress relief therapy; and a skin care regime.

11. The system of claim 9, wherein the facial skin analysis application further comprises:
   a registration circuitry configured to register each of the plurality of vehicles with the facial skin analysis application;
   a database of subscriber information, the subscriber information including the user profile of each vehicle seat occupant of each of the plurality of vehicles;
   wherein the facial skin analysis application further correlates the subscriber information with the facial skin conditions of each identified vehicle seat occupant in determining the facial skin treatment recommendation of the identified vehicle seat occupant.

12. The system of claim 11, wherein the data lake is configured to store the facial skin images of each of the identified vehicle seat occupants of each of the plurality of vehicles.

13. The system of claim 11, comprising:
   wherein the registration circuitry is further configured to register a vehicle occupant travelling in any of the plurality of vehicles with the facial skin analysis application through a smart device of the vehicle occupant and retrieve a user profile from the smart device;
   wherein the facial skin analysis application is further configured to:
   receive and store current timestamped facial skin images of the registered vehicle occupant in a facial skin analysis application memory when the registered vehicle occupant travels in any of the plurality of vehicles;
   detect feature changes between the current timestamped facial skin images and previously stored facial skin images of the registered vehicle occupant;
   request a search by the skin data AI analytics circuitry for information related to the feature changes;
   wherein the facial skin data AI analytics circuitry is further configured to form search queries based on the feature changes and transmit the search queries to the data lake;
   wherein the data lake is configured to receive the search queries, search for facial skin information from a plurality of sources for matches to the search queries and transmit the matches to the facial skin data AI analytics circuitry;
   wherein the facial skin data AI analytics circuitry is further configured to analyze the matches and determine a skin condition, treatment options for the skin condition and facial skincare product information related to the skin condition;
   wherein the facial skin analysis application is further configured to receive the skin condition, treatment options for the skin condition and facial skincare product information related to the skin condition and correlate the skin condition, treatment options for the skin condition and facial skincare product information related to the skin condition with the user profile;
   wherein the treatment recommendation circuitry is configured to generate a facial skin treatment recommendation;
   wherein the facial skin analysis application is further configured to transmit the facial skin treatment recommendation of the registered vehicle occupant to the smart device of the registered vehicle occupant.

14. The system of claim 13, wherein the registration circuitry is further configured to:
   register the vehicle occupant by receiving a public key from the smart device;
   request personal information from the vehicle occupant including age, weight, gender, ethnic origins, previous skin and medical diseases of the vehicle seat occupant;
   request lists of preferred medical practitioners, dermatologists, cosmetologists and skin care professionals, and retail outlets; and
   store the public key, personal information and lists in a subscriber database.

15. The system of claim 13, wherein the previously timestamped skin facial images are from a time period preferably in the range of one hour to five years, more preferably in the range of one hour to one year, most preferably in the range of one hour to two months.

16. The system of claim 9, further comprising:
   wherein the plurality of sensors include at least one of weight sensors located in each seat, fingerprint sensors on the steering wheel, a fingerprint reader on the user interface, a breathalyzer, audio sensors and heart rate sensors;
   wherein the identity circuitry is further configured to match information from the at least one sensor with previously stored sensor profiles of vehicle seat occupants to identify a current vehicle seat occupant and retrieve the user profile of the current vehicle seat occupant, the user profile including the age, weight and height of the current vehicle seat occupant; and
   wherein the CPU adjusts the field of view of the camera of the current vehicle seat occupant based on the height.

17. A non-transitory computer readable medium having instructions stored therein that, when executed by one or more processor, cause the one or more processors to perform a method for improving facial skin conditions using vehicle cameras, comprising:
   imaging a facial skin of at least one vehicle seat occupant by at least one vehicle camera each time the vehicle occupant occupies a seat in the vehicle;
   storing images of the facial skin with timestamps of the images;
   comparing each current image with at least one stored image of the vehicle seat occupant having an earlier timestamp;
   detecting changes between the current image and the at least one stored image having the earlier timestamp;
   accessing facial skin data which includes facial skin conditions based on at least one of age, gender, ethnic origins and medical diseases affecting the facial skin;
   matching the changes to at least one facial skin condition;
   accessing treatment options for the at least one facial skin condition;
   accessing facial skincare product information for the at least one facial skin condition;
   determining a facial skin treatment recommendation based on the at least one facial skin condition, the treatment options and the facial skincare product information; and
   notifying the vehicle seat occupant of the facial skin changes, the at least one facial skin condition and the facial skin treatment recommendation.

18. The non-transitory computer readable medium method of claim 17, further comprising:
   transmitting the facial skin images and the changes by an onboard communications circuitry of the vehicle to a facial skin analysis application;

transmitting the facial skin images to a data lake;
requesting, by the facial skin analysis application, a search of the data lake for facial skin information related to the facial skin images and the facial skin changes;
receiving the request by a facial skin data artificial intelligence (AI) analytics circuitry;
querying, by the facial skin data AI analytics circuitry, the data lake for information relating to the facial skin images and the facial skin changes, treatment options and skincare products;
searching, within the data lake, unstructured data and structured databases for matches to the query;
retrieving, by the facial skin data AI analytics circuitry, the matches to the query;
analyzing, by the facial skin data AI analytics circuitry, the matches to determine a skin condition, treatment options for the skin condition and facial skincare product information related to the skin condition;
receiving, by the facial skin analysis application, the skin condition, treatment options for the skin condition and facial skincare product information;
accessing a user profile of a vehicle seat occupant;
correlating the user profile with the treatment options and facial skincare product information to generate the facial skin treatment recommendation;
transmitting, by the facial skin analysis application, the facial skin treatment recommendation to the onboard communications circuitry of the vehicle;
receiving the facial skin treatment recommendation by the onboard communications circuitry; and
updating the memory of the vehicle.

19. The non-transitory computer readable medium method of claim 18, further comprising:
registering, through a smart device of the vehicle seat occupant, with the facial skin analysis application;
creating a user profile including age, weight, gender, ethnic origins, previous skin and medical diseases of the vehicle seat occupant;
receiving, by the facial skin analytics application, the facial skin images and the changes from an onboard communication circuitry of the vehicle;
transmitting the facial skin images to the data lake;
requesting, by the facial skin analysis application, a search related to the facial skin images and changes;
receiving, by the facial skin data artificial intelligence (AI) analytics program, the request;
querying, by the facial skin data AI analytics circuitry, the data lake for information related to the facial skin images and the changes, treatment options and skincare products;
searching, within the data lake, unstructured data and structured databases for matches to the query;
retrieving, by the facial skin data AI analytics circuitry, the matches to the query;
analyzing, by the facial skin data AI analytics circuitry, the matches to the query to determine a skin condition, treatment options for the skin condition and facial skincare product information related to the skin condition;
receiving, by the facial skin analysis application, the skin condition, treatment options for the skin condition and facial skincare product information;
accessing the user profile of the vehicle seat occupant;
correlating the user profile with the treatment options and facial skincare product information to generate the facial skin treatment recommendation; and
transmitting the recommendation to the smart device of the registered vehicle seat occupant.

20. The non-transitory computer readable medium method of claim 19, wherein registering with the facial skin analysis application by the vehicle seat occupant further comprises:
creating public and private pair keys with a smart device of the vehicle seat occupant;
transmitting the public key to the facial skin analysis application; and
providing a list of preferred medical practitioners, dermatologists, cosmetologists and skin care professionals, and retail outlets.

* * * * *